US009400874B2

(12) United States Patent
Powell et al.

(10) Patent No.: US 9,400,874 B2
(45) Date of Patent: Jul. 26, 2016

(54) SYSTEMS AND METHODS FOR VIEWING PATIENT DATA

(75) Inventors: William Cameron Powell, San Antonio, TX (US); Stephen Trey Moore, San Antonio, TX (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 51 days.

(21) Appl. No.: 13/376,735

(22) PCT Filed: Jun. 8, 2010

(86) PCT No.: PCT/US2010/037728
§ 371 (c)(1),
(2), (4) Date: Dec. 7, 2011

(87) PCT Pub. No.: WO2010/144413
PCT Pub. Date: Dec. 16, 2010

(65) Prior Publication Data
US 2012/0075103 A1 Mar. 29, 2012

Related U.S. Application Data

(60) Provisional application No. 61/185,096, filed on Jun. 8, 2009.

(51) Int. Cl.
G06F 19/26 (2011.01)
G06F 19/00 (2011.01)
A61B 5/0452 (2006.01)
A61B 5/00 (2006.01)
A61B 5/0468 (2006.01)

(52) U.S. Cl.
CPC .......... *G06F 19/3487* (2013.01); *A61B 5/0022* (2013.01); *A61B 5/0452* (2013.01);
(Continued)

(58) Field of Classification Search
CPC ............. A61B 5/0402; A61B 5/04011; A61B 5/04012; A61B 5/044; A61B 5/0452; A61B 5/0468; A61B 5/0472; A61B 5/743; A61B 5/7435; A61B 5/7455; A61B 5/746; A61B 5/7475; A61B 5/748; A61B 5/0002; A61B 8/461; A61B 8/465; A61B 8/469; G06T 2207/20092; G06T 2207/30048
USPC ....................................... 340/573.1
See application file for complete search history.

(56) References Cited

U.S. PATENT DOCUMENTS 3,793,626 A * 2/1974 Zambuto .................. 340/870.09
3,972,320 A * 8/1976 Kalman ........................ 600/519
(Continued)

FOREIGN PATENT DOCUMENTS

CN 1681272 A 10/2005
CN 101137977 A 3/2008
(Continued)

OTHER PUBLICATIONS

Authorized Officer Yolaine Cussac, International Preliminary Report on Patentability for Application No. PCT/US2010/037728, dated Dec. 22, 2011, 7 pages.
(Continued)

*Primary Examiner* — Steven Lim
*Assistant Examiner* — Benyam Haile
(74) *Attorney, Agent, or Firm* — Fish & Richardson P.C.

(57) ABSTRACT

Methods of measuring features of a digitally generated waveform include communicating patient data to a device that is remote from a source of the patient data, generating the waveform on a touch-screen display of the device, and measuring along an axis of the waveform. The measuring includes generating a first point corresponding to the waveform based on contact with the touch-screen display, generating a second point corresponding to the waveform based on contact with the touch-screen display, automatically measuring a distance between the first point and the second point along the axis upon generation of the second point, and displaying a value corresponding to the distance on the touch-screen display.

26 Claims, 14 Drawing Sheets

(52) U.S. Cl.
CPC ........... *G06F19/3418* (2013.01); *A61B 5/0006* (2013.01); *A61B 5/0468* (2013.01); *A61B 5/74* (2013.01); *A61B 5/748* (2013.01); *A61B 5/7435* (2013.01); *A61B 5/7455* (2013.01); *G06F 19/34* (2013.01); *G06F 19/345* (2013.01)

(56) References Cited

U.S. PATENT DOCUMENTS

| | | | |
|---|---|---|---|
| 6,537,214 B1* | 3/2003 | Hood et al. | 600/300 |
| 6,893,396 B2 | 5/2005 | Schulze et al. | |
| 7,137,074 B1* | 11/2006 | Newton et al. | 715/835 |
| 7,346,174 B1 | 3/2008 | Smith | |
| 8,209,002 B2* | 6/2012 | Vajdic et al. | 600/512 |
| 2002/0052559 A1 | 5/2002 | Watrous | |
| 2002/0151812 A1 | 10/2002 | Scheiner et al. | |
| 2007/0179356 A1 | 8/2007 | Wessel | |
| 2007/0191740 A1* | 8/2007 | Shertukde et al. | 600/586 |
| 2007/0239003 A1 | 10/2007 | Shertukde et al. | |
| 2008/0188765 A1 | 8/2008 | Stolarski et al. | |
| 2009/0054743 A1 | 2/2009 | Stewart | |
| 2009/0088655 A1 | 4/2009 | Vajdic et al. | |
| 2010/0191073 A1* | 7/2010 | Tarassenko et al. | 600/301 |

FOREIGN PATENT DOCUMENTS

| | | |
|---|---|---|
| JP | 64043907 A | 2/1989 |
| JP | 05317269 A | 12/1993 |
| JP | 11089802 A | 4/1999 |
| JP | 2003319913 A | 11/2003 |
| JP | 2004254930 A | 9/2004 |
| JP | 2008539988 T | 11/2008 |
| WO | WO2006078954 A1 | 7/2006 |
| WO | WO2009034507 A1 | 3/2009 |
| WO | WO2010144413 A1 | 12/2010 |

OTHER PUBLICATIONS

Plaintiffs' Complaint for Patent Infringement, *Airstrip Technologies, Inc. et al. v. mVISUM, Inc.*, Civil Action No. 1:12-cv-07776-JFK, United States District Court for the Southern District of New York, Document 1, filed Oct. 18, 2012, 30 pages.

Defendant's Answer and Counterclaim, *Airstrip Technologies, Inc. et al. v. mVISUM, Inc.*, Civil Action No. 1:12-cv-07776-JFK, United States District Court for the Southern District of New York, Document 29, filed Apr. 5, 2013, 13 pages.

GE Healthcare, "Web Viewer and Pocket Viewer," 2007, retrieved from http://www3.gehealthcare.com/~/media/Downloads/us/Product/Product-Categories/Patient-Monitoring/Careports/Mobile-Viewers/GEHealthcare-Web-Viewer-Pocket-Viewer-ProductSpec. pdf?Parent=%7B1ED25767-3F69-413B-8C56-3DDEA5CEF31F%7D, 4 pages.

Edward H. Schmuhl et al., "HP PalmVue: A New Healthcare Information Product," Hewlett-Parkard Journal, Article 8, Jun. 1996, retrieved from http://www.hpl.hp.com/hpjournal/96jun/jun96a8.pdf, pp. 12-17.

MobileInfo, "Data Critical's StatView™ Alarm Notification System," Jun. 2000, retrieved from http://www.mobileinfo.com/Applications_Vertical/Healthcare_Applications/StatView.htm, 2 pages.

Telecompaper, "Data Critical Launches Rhythmstat XL Medical System," Jan. 8, 1998, retrieved from http://www.telecompaper.com/news/data-critical-launches-rhythmstat-xl-medical-system--26725, 2 pages.

U.S. Food and Drug Administration, Protecting and Promoting Your Health, "MAUDE Adverse Event Report: Data Critical Corp. Impactpaging System," Nov. 19, 2000, retrieved on Apr. 8, 2013 from <www.accessdata.fda.gov/scripts/cdrh/cfdocs/cfmaude/detail.cfm?mdrfoi__id=312735>, 2 pages.

Department of Health & Human Services, Food and Drug Administration, Center for Devices and Radiological Health, 510(k) Summary and approval letter for FlexView™ Clinical Monitoring System (K003998), Mar. 7, 2001, 4 pages.

Department of Health & Human Services, Food and Drug Administration, Center for Devices and Radiological Health, 501(k) Summary and approval letter AlamView™ Wireless Data Network System (K010912), Apr. 5, 2001, 4 pages.

Department of Health & Human Services, Food and Drug Administration, Center for Devices and Radiological Health, 510(k) Summary and approval letter for Agilent Information Center (AIC) Software Release D.0 (K011093), May 1, 2001, 5 pages.

Department of Health & Human Services, Food and Drug Administration, Center for Devices and Radiological Health, 510(k) Summary and approval letter for Mobile-PatientViewer™ (K011436), Jul. 5, 2001, 5 pages.

Department of Health & Human Services, Food and Drug Administration, Center for Devices and Radiological Health, 510(k) Summary and approval letter for FlexView™ Clinical Monitoring System (K011999), Jul. 24, 2001, 4 pages.

Department of Health & Human Services, Food and Drug Administration, Center for Devices and Radiological Health, 510(k) Summary and approval letter for AlarmView™ Wireless Data Network System (K012005), Jul. 24, 2001, 4 pages.

Department of Health & Human Services, Food and Drug Administration, Center for Devices and Radiological Health, 510(k) Summary and approval letter for AlarmView™ Wireless Data Network System (K013156), Oct. 19, 2001, 4 pages.

Department of Health & Human Services, Food and Drug Administration, Center for Devices and Radiological Health, 510(k) Summary and approval letter for Datex-Ohmeda S/5 Web Viewer, Datex-Ohmeda S/5 Pocket Viewer and Datex-Ohmeda S/5 Cellular Viewer with L-WEB04 software (K052975), Jan. 20, 2006, 7 pages.

Department of Health & Human Services, Food and Drug Administration, Center for Devices and Radiological Health, 510(k) Summary and approval letter for Web Viewer, Pocket Viewer and Cellular Viewer with L-WEB05 software (K061994), Aug. 11, 2006, 4 pages.

Department of Health & Human Services, Food and Drug Administration, Center for Devices and Radiological Health, 510(k) Summary and approval letter for RhythmStat XL System (K971650), Dec. 4, 1997, 9 pages.

Department of Health & Human Services, Food and Drug Administration, Center for Devices and Radiological Health, 510(k) Summary and approval letter for Cardio-Pager™ System (K973527), Mar. 31, 1998, 6 pages.

Department of Health & Human Services, Food and Drug Administration, Center for Devices and Radiological Health, 510(k) Summary and approval letter for Hewlett-Packard M2605A Viridia Wave Viewer (K974567), Jan. 20, 1998, 5 pages.

Department of Health & Human Services, Food and Drug Administration, Center for Devices and Radiological Health, 510(k) Summary and approval letter for StatView™ System (K990378), Sep. 20, 1999, 6 pages.

Department of Health & Human Services, Food and Drug Administration, Center for Devices and Radiological Health, 510(k) Summary and approval letter for AlarmView™ System (K992848), Nov. 19, 1999, 6 pages.

First Office Action for Chinese Patent Application No. 201080035108.4, Jan. 21, 2014, 22 pages.

Japan Patent Office, Notice of Reasons for Rejection for Japanese Patent Application No. 2012-515051, Jun. 26, 2014, 4 pages.

Second Office Action for Chinese Patent Application No. 201080035108.4, Aug. 29, 2014, 16 pages.

Authorized Officer Blaine R. Copenheaver, Notification of Transmittal of the International Search Report and the Written Opinion of the International Searching Authority for PCT/US2010/037728, dated Aug. 11, 2010, 9 pages.

Patent Examination Report No. 1 for AU2010258983, dated Oct. 22, 2014, 4 pages.

Japan Patent Office, Final Notice of Reasons for Rejection for Japanese Patent Application No. 2012-515051, dated Mar. 4, 2015, 4 pages.

European Search Report for Application No. 10786670.9, dated Apr. 18, 2016, 4 pages.

\* cited by examiner

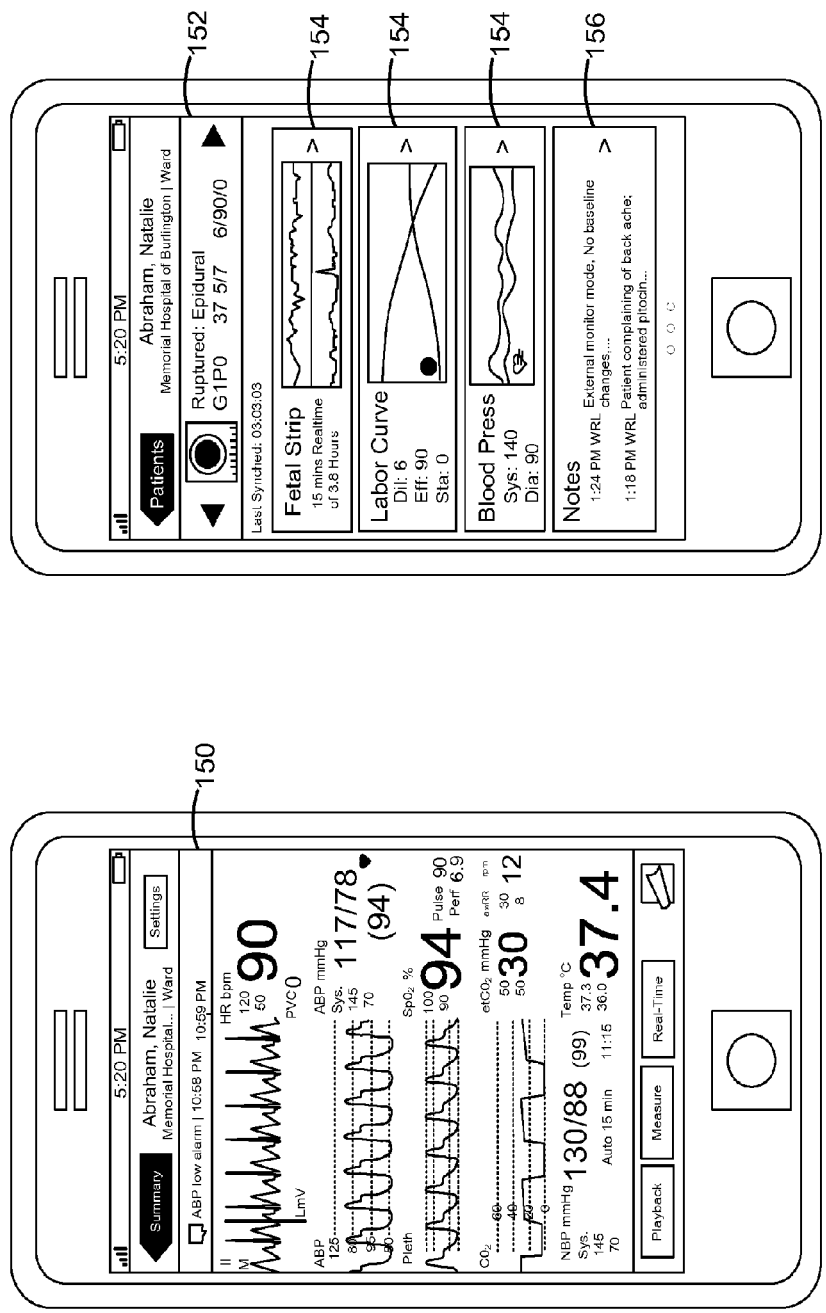

SYSTEMS AND METHODS FOR VIEWING PATIENT DATA

CROSS-REFERENCE TO RELATED APPLICATIONS

This application is the U.S. national stage application under 35 USC §371 of International Application Number PCT/US2010/037728 filed on Jun. 8, 2010, which claims the benefit of Provisional Application No. 61/185,096 filed on Jun. 8, 2006, the entire contents of which are hereby incorporated by reference.

FIELD

This invention generally relates to systems and methods for transmitting, receiving and displaying data and/or information over wireless communication and data processing devices, and more specifically to a system and method for collecting, uploading, transmitting, receiving, downloading, manipulating, and displaying medical patient data and/or information to a remote device operable by a health care provider.

BACKGROUND

While physicians and other health care providers currently utilize a large number of products and systems that benefit from advances in wireless communication technology, there are still significant limitations to the information that can be transmitted, received, and displayed over these devices in a practical and efficient manner. There are many limitations that are intrinsic to mobile devices, especially those constraints related to speed, performance, memory, and display size. In addition, because of the critical nature of medical data, it is important that the technology work reliably and efficiently over potentially low speed, low bandwidth, and sometimes intermittent wireless connections.

Efforts have been made in the past to transmit medical information through various telecommunication means to health care professionals for review and analysis. Some such efforts are outlined in commonly assigned U.S. patent application Ser. No. 11/301,348, filed on Dec. 12, 2005, the disclosure of which is expressly incorporated herein by reference in its entirety for all purposes. Such examples utilize wireless data communication technologies to transmit medical information to health care providers, or to condition data such that it may be useful for remote monitoring purposes.

SUMMARY

In one aspect, the present invention provides a method of measuring features of a digitally generated waveform, the method including communicating patient data to a device that is remote from a source of the patient data, generating the waveform on a touch-screen display of the device, and measuring along an axis of the waveform. In some aspects, the measuring includes generating a first point corresponding to the waveform based on contact with the touch-screen display, generating a second point corresponding to the waveform based on contact with the touch-screen display, automatically measuring a distance between the first point and the second point along the axis upon generation of the second point, and displaying a value corresponding to the distance on the touch-screen display.

In some aspects, the value includes a time value.
In some aspects, the value includes a voltage value.

In some aspects, the method further includes generating a digital caliper in the touch-screen display, the caliper including a first and a second jaw that are movable along the axis, the first point being generated based on an intersection between the first jaw and the waveform, and the second point being generated based on an intersection between the second jaw and the waveform. The caliper is generated based on a user demand.

In some aspects, the axis includes one of a time axis and a voltage axis.

In some aspects, the waveform corresponds to one of an electrocardiogram (ECG), a blood pressure, an oxygen saturation, and an end-tidal $CO_2$.

In some aspects, the method further includes moving at least one of the first point and the second point along the axis, and updating the value in real-time based on movement of the at least one of the first point and the second point along the axis.

In some aspects, the method further includes storing the value in a memory of the device.

In some aspects, the method further includes transmitting the value to a patient information system located at a facility.

In other aspects, the present invention provides a method of monitoring patient data using a device. In some aspects, the method includes communicating patient data to the device, the device being remote from a source of the patient data, generating a waveform on a display of the device based on the patient data, identifying an occurrence of a waveform feature, and generating a sound based on the occurrence of the waveform feature.

In some aspects, the generating a sound comprises repetitively generating the sound in response to periodic occurrences of the waveform feature.

In some aspects, the generating a sound comprises generating a persistent sound.

In some aspects, the method further includes storing an audio file in memory of the device, and retrieving the audio file from memory based on generating the waveform, the sound being generated based on the audio file.

In some aspects, the method further includes storing a plurality of audio files in memory of the device, and selecting an audio file from the plurality of audio files based on a type of the waveform, the sound being generated based on the audio file.

In some aspects, the waveform feature includes one of a spike, a peak, a trough and a flat line.

In some aspects, the waveform corresponds to one of a heart rate, a blood pressure, an oxygen saturation, and an end-tidal $CO_2$.

In still other aspects, the present invention provides a method of notifying a user of an alert. In some aspects, the method includes generating an alert based on patient data, providing the alert to a third-party notification service, forwarding the alert to a device, the device being remote from a source of the patient data, receiving the alert at the device, and presenting an indication of the alert on a display of the device.

In some aspects, the alert is generated at an information system that is resident at a facility, at which the patient data is collected.

In some aspects, the alert is generated at a data management system that is remote from the source of the patient data.

In some aspects, the alert corresponds to an application that is resident on the device, and that is executable using the device. In some aspects, the application is dormant when the alert is received at the device.

In some aspects, the indication includes at least one of a badge associated with an application icon, and an alert summary. The alert summary provides patient information. In some aspects, the method includes selecting the alert summary, and displaying detailed alert information on the display of the device in response to the selecting.

Other aspects of the present invention provide a computer-readable storage medium encoded with a computer program comprising instructions that, when executed, operate to cause one or more processors to perform one or more of the methods provided herein.

Still other aspects of the invention provide a system including one or more processors, and a computer-readable medium coupled to the one or more processors having instructions stored thereon which, when executed by the one or more processors, cause the one or more processors to perform one or more of the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments are set forth in the accompanying drawings and the description below. Other features, objects, and advantages will be apparent from the description and drawings, and from the claims.

DESCRIPTION OF DRAWINGS

FIGS. 5A-5H provide exemplar screenshots on an exemplar mobile device in accordance with the present disclosure.

Like reference symbols in the various drawings indicate like elements.

DETAILED DESCRIPTION

The present disclosure provides a healthcare provider with secure, remote access to patient data. The present disclosure builds on that of commonly assigned U.S. patent application Ser. No. 11/301,348, filed on Dec. 12, 2005, the disclosure of which is expressly incorporated herein by reference in its entirety for all purposes. U.S. patent application Ser. No. 11/301,348 claims the benefit of U.S. Prov. App. No. 60/641,057, filed on Jan. 3, 2005, the disclosure of which is also expressly incorporated herein by reference in its entirety for all purposes. The present disclosure also builds on that of commonly assigned U.S. patent application Ser. No. 11/301,348, filed on Dec. 12, 2005, the disclosure of which is expressly incorporated herein by reference in its entirety for all purposes. For purposes of the instant description, and by way of non-limiting example, implementations of the present disclosure will be described in the context of patient data corresponding to maternity patients (e.g., obstetric (OB) patient). Implementations of the present disclosure are applicable to any variety of patients and corresponding patient data.

Figure 1:
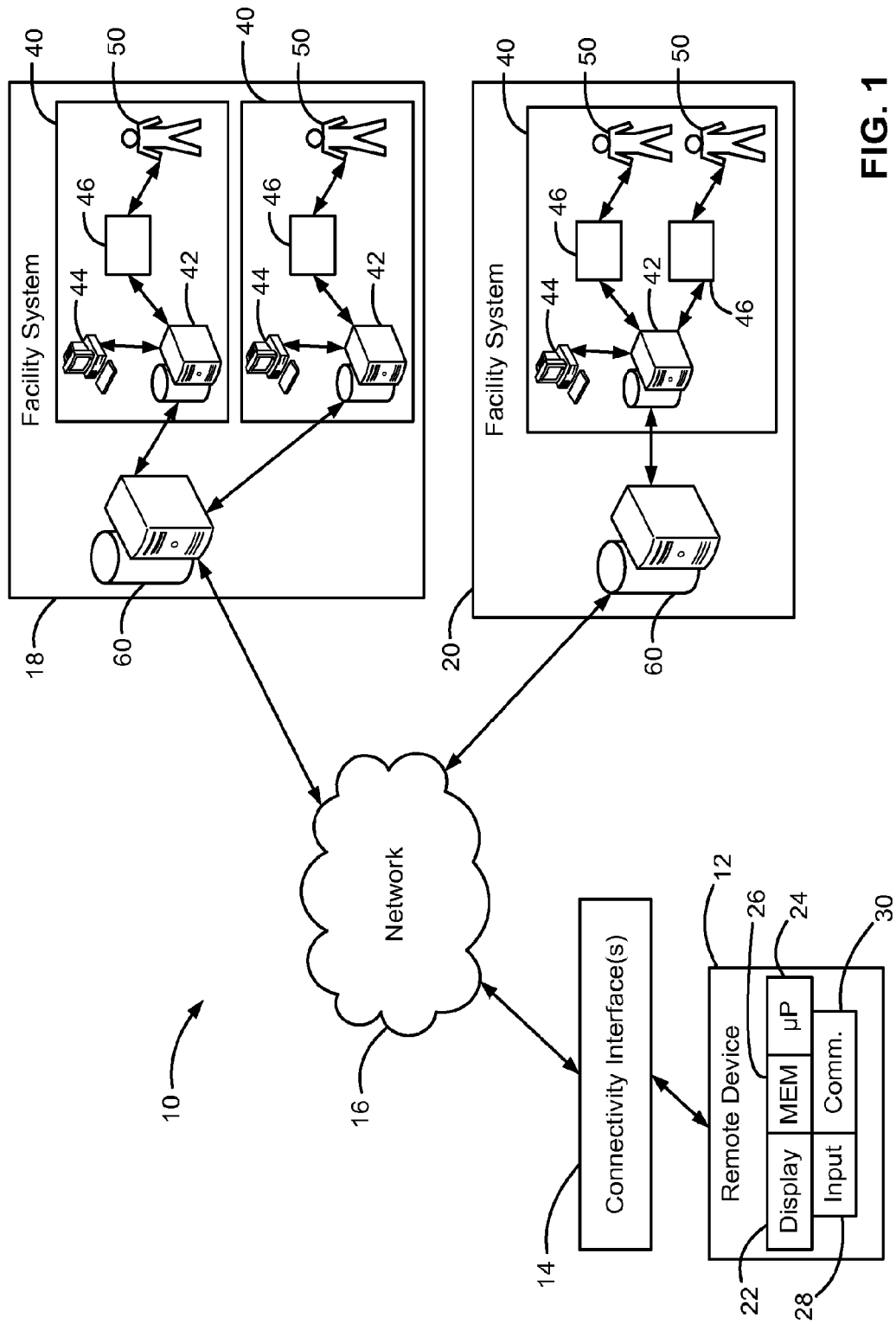
FIG. 1 is a schematic illustration of an exemplar system architecture in accordance with the present disclosure.

Referring now to FIG. 1, an exemplar system architecture 10 is illustrated, and includes a remote device 12, connectivity interface(s) 14, a network 16, a first facility system 18, and a second facility system 20. As discussed in further detail herein, data is transferred from each of the first and second facility systems 18, 20 through the network 16 and connectivity interface(s) 14 for presentation, or display on the remote device 12. Further, data can be transferred from the remote device 12 through the connectivity interface(s) 14 and network 16 to each of the first and second facility systems 18, 20. Although a single remote device 12 is illustrated, it is contemplated that one or more remote devices 12 can communicate with each of the first and second facility systems 18, 20 through the network 16 and connectivity interface(s) 14. Similarly, although two facility systems are illustrated, the present disclosure can be implemented with one or more facility systems.

The remote device 12 can include any number of exemplar devices. Such exemplar devices include, but are not limited to, a mobile phone, a smartphone, a personal digital assistant (PDA), a laptop, a tablet personal computer (PC), a desktop PC, and/or combinations thereof. The remote device 12 includes a display 22, a processor 24, memory 26, an input interface 28, and a communication interface 30. The processor 24 can process instructions for execution of implementations of the present disclosure. The instructions can include, but are not limited to, instructions stored in the memory 26 to display graphical information on the display 22. Exemplar displays include, but are not limited to, a thin-film-transistor (TFT) liquid crystal display (LCD), or an organic light emitting diode (OLED) display.

The memory 26 stores information within the remote device 12. In some implementations, the memory 26 can include a volatile memory unit or units, and/or a non-volatile memory unit or units. In other implementations, removable memory can be provided, and can include, but is not limited to, a memory card. Exemplar memory cards can include, but are not limited to, a secure digital (SD) memory card, a mini-SD memory card, a USB stick, and the like.

The input interface 28 can include, but is not limited to, a keyboard, a touchscreen, a mouse, a trackball, a microphone, a touchpad, and/or combinations thereof. In some implementations, an audio codec (not shown) can be provided, which receives audible input from a user or other source through a microphone, and converts the audible input to usable digital information. The audio codec can generate audible sound, such as through a speaker that is provided with the remote device 12. Such sound may include, but is not limited to, sound from voice telephone calls, recorded sound (e.g., voice messages, music files, etc.), and sound generated by applications operating on the remote device 12.

The remote device 12 may communicate wirelessly through the communication interface(s) 14, which can include digital signal processing circuitry. The communication interface(s) 14 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the remote device can be capable of short-range communication using features including, but not limited to, Bluetooth and/or WiFi transceivers (not shown).

The remote device 12 communicates with the network 16 through the connectivity interface(s) 14. The connectivity interface(s) 14 can include, but is not limited to, a satellite receiver, cellular network, a Bluetooth system, a Wi-Fi system (e.g., 802.x), a cable modem, a DSL/dial-up interface, and/or a private branch exchange (PBX) system. Each of these connectivity interfaces 14 enables data to be transmitted to/from the network 16. The network 16 can be provided as a local area network (LAN), a wide area network (WAN), a wireless LAN (WLAN), a metropolitan area network (MAN), a personal area network (PAN), the Internet, and/or combinations thereof.

Figure 2:
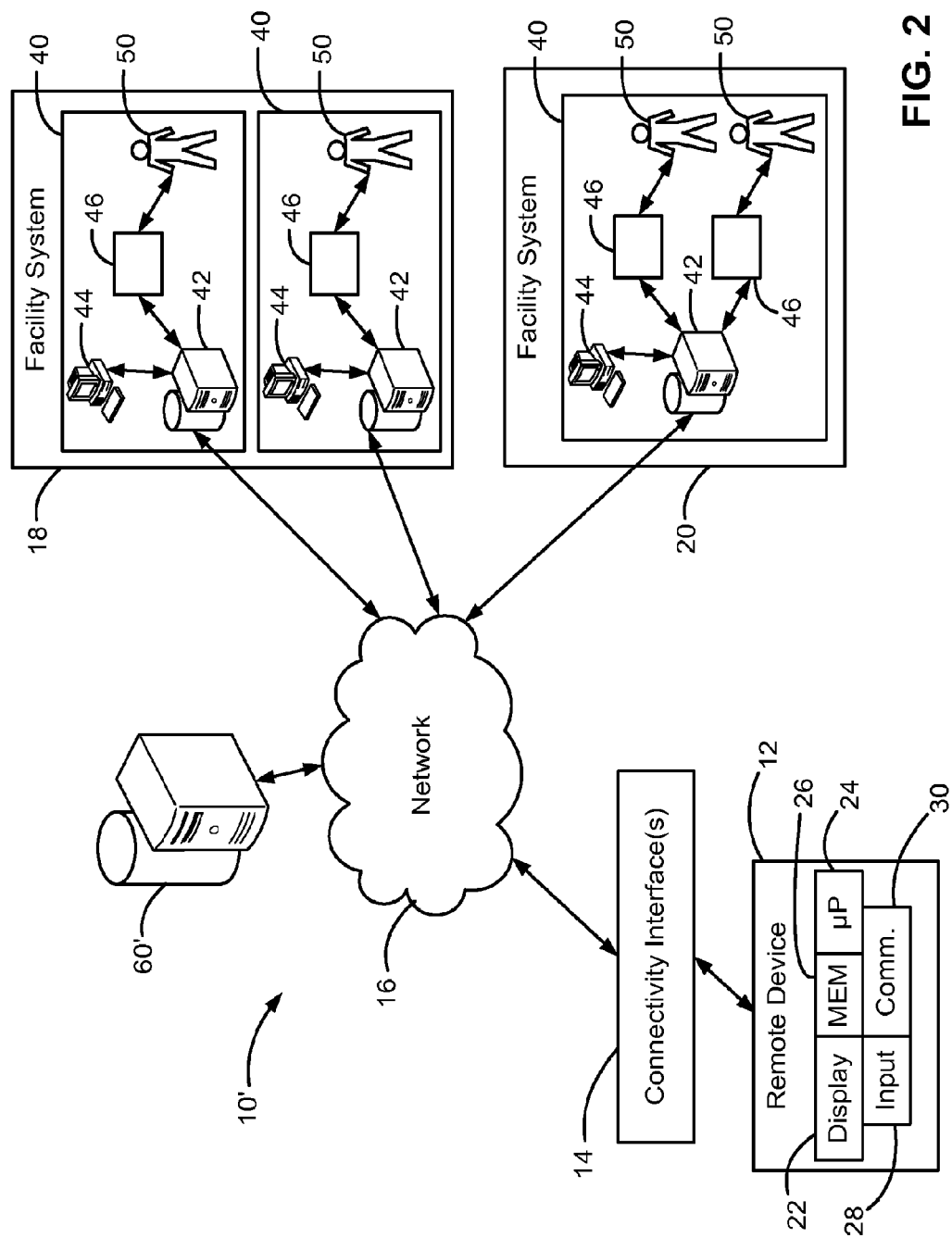
FIG. 2 is a schematic illustration of another exemplar system architecture in accordance with the present disclosure.

In the exemplar systems of FIGS. 1 and 2, the first facility system 18 includes a plurality of facilities 40, and the second facility system 20 includes a facility 40. It is contemplated that each facility system 18, 20 can include one or more facilities, and is not limited to the exemplar arrangement described herein. In the case of multiple facilities, the facilities can be remotely located from one another, and/or can be located at a common location, or site (e.g., separate departments in a common building). Each facility system 18, 20 can be provided as a medical care system, for example, which medical care system can include one or more hospitals, hospital systems, clinics, physician offices, and the like.

Each facility 40 includes an associated information system 42, computer interface(s) 44, and patient monitoring device(s) 46. Exemplar information systems can include, but are not limited to, a clinical information system (CIS), and/or a hospital information system (HIS). Each information system 42 can be provided as a server, and supports the acquisition, storage, modification, and distribution of clinical information, such as patient data, throughout the facility 40 and/or facility system 18, 20. Exemplar information systems include, but are not limited to, the Integriti Enterprise Wide CIS, the QS Perinatal CIS, and/or the QS Critical Care CIS, each provided by General Electric (GE), the OBiX Perinatal Data System provided by Clinical Computer Systems, Inc., the IntelliVue Clinical Information Portfolio (ICIP), Critical Care and/or OB TraceVue Perinatal Data System provided by Royal Philips Electronics, the Essentris Perinatal, Acute Care and/or Critical Care systems provided by CliniComp International, Inc., the CALM Perinatal Data System provided by LMS Medical Systems, the Horizon Lab, Medical Imaging, Cardiology, Emergency Care and/or Perinatal Care provided by McKesson Corporation, and/or the NaviCare WatchChild System provided by Hill-Rom. Each information system 42 can communicate with one or more ancillary information systems (not shown) that can include, but are not limited to, a pharmacy management system, a laboratory management system, and/or a radiology management system. Although the exemplar system architecture 10 includes an information system 42 located at each facility 40, it is contemplated that the facilities 40 can communicate with a common information system 42 that is remotely located from either facility 40, or that is located at one of the facilities 40 within the facility system 18, 20.

The computer interface 44 can communicate with the information system 42 to enable access to information that is stored within, and managed by the information system 42. The computer interface 44 can include, but is not limited to, a personal computer (PC) (e.g., desktop, laptop, or tablet). Although a single computer interface 44 is illustrated in the exemplar architectures described herein, it is contemplated that one or more computer interfaces 44 can communicate with the information system 42. Communication between each computer interface 44 and the information system 42 can be achieved via a direct connection, or remotely through a network (not shown) that can include, but is not limited to, a LAN, a WAN, a WLAN, and/or the Internet.

Each patient monitoring device 46 monitors physiological characteristics of a particular patient 50, and generates data signals based thereon. Exemplar patient monitoring devices include, but are not limited to, maternal/fetal heart rate monitors, blood pressure monitors, respiratory monitors, vital signs monitors, electrocardiogram monitors, oximetry and/or anesthesia monitors. Exemplar patient monitoring devices can include, but are not limited to the Corometric Series Monitors, DINAMAP Series Monitors, DASH Series Monitors, and/or Solar Series monitors provided by GE Healthcare, IntelliVue and/or SureSigns Series patient monitors, and/or Avalon Series Fetal Monitors provided by Royal Philips Electronics, and/or Infinity Series patient monitors provided by Draeger Medical. The data signals are communicated to the information system 42, which collects patient data based thereon, and stores the data to a patient profile that is associated with the particular patient. Although a single patient monitoring device 46 is illustrated per each patient 50, it is contemplated that multiple patient monitoring devices 46 can monitor a particular patient 50. The patient monitoring device(s) 46 can communicate with the information system 42 via a direct connection, or remotely through a network (not shown) that can include, but is not limited to, a LAN, a WAN, a WLAN, and/or the Internet.

The patient data is made available for display on the computer device 44. A healthcare provider (e.g., a nurse and/or physician) can augment the patient data by inputting patient information that is also stored to the information system 44. More specifically, the healthcare provider can input patient information corresponding to a particular patient 50, which patient information can be stored to the patient profile. By way of one non-limiting example, a nurse can input nursing notes, which nursing notes can be stored to the patient profile in the information system. As used herein, the term patient information includes any information corresponding to a patient that is input and stored to the information system 42 through the computer interface 44. Patient information is discussed in further detail below.

As discussed above, each information system 42 stores patient data that can be collected from the patient monitoring devices 46, as well as additional patient information, that can include information that is input by a healthcare provider. The information system 46 communicates the patient data and/or the additional patient data to a data management system (DMS) 60. The DMS 60 can be provided as a server, or a virtual server, that runs server software components, and can include data storage including, but not limited to, a database and/or flat files. In the exemplar system architecture of FIG. 1, each facility system 18, 20 includes a corresponding DMS 60. In such an arrangement, each information system 42 communicates patient data, and/or additional patient data to the DMS 60. Furthermore, and as discussed in further detail below, the DMS 60 can communicate ancillary information to the information system 42. Communication between the DMS 60 and the information system(s) 42 can be achieved via a direct connection, or remotely through a network (not shown) that can include, but is not limited to, a LAN, a WAN, a WLAN, and/or the Internet.

A DMS 60 corresponding to a particular facility system can be remotely located from any of the facilities 40 of the facility system 18, 20, or can be located at a particular facility 40 of the facility system 18, 20. In the exemplar system architecture of FIG. 1, the DMS 60 is remotely located from either facility 40 within each of the facility systems 18, 20. It is contemplated, however, that the DMS 60 can be located at one of the facilities 40, and remote from the other facility 40.

In the exemplar system architecture of FIG. 2, a common DMS 60' is provided. The common DMS 60' is common to various facility systems 18, 20, and is not associated with a particular facility system 18, 20. Each information system 42 communicates with the DMS 60' via a direct connection, or remotely through a network (not shown) that can include, but is not limited to, a LAN, a WAN, a WLAN, and/or the Internet. In the exemplar arrangement of FIG. 2, the DMS 60' communicates with each of the information systems 42 through the network 16. The information systems 42 communicate patient data and/or patient information to the DMS 60', and the DMS 60' can communicate ancillary information to the information system 42, as discussed in further detail below.

In the exemplar system architecture of FIG. 1, the facility 40, or facility system 18, 20 installs the DMS 60 as a local DMS, and the DMS 60 sits at the local site with other servers that can include, but are not limited to, the information system 42. In some implementations, the DMS 60 can be sectioned off, or separated from a logical network perspective, but still physically exists with the other servers that belong to the respective facility 40. Server components are installed on the DMS 60, which components can include, but are not limited to, a database component, a database synchronization component, a web services component, and/or a structured query language (SQL) component. An information system interface can also be installed on the DMS 60, and functions as the interface to the information system 42. By way of non-limiting example, the information system interface can include OBLink, provided by GE Healthcare. In some implementations, the DMS 60 can be arranged in a multiple server configuration, in which one server only hosts web service related components and is logically segregated, and another server has the remaining necessary server components installed.

The exemplar system architecture of FIG. 2, provides for the remote location of data collection at the DMS 60'. In such implementations, the DMS 60' can be provided at a third-party site, remote from any of the facilities 40, or facility systems 18, 20. The third-party functions as a DMS host, and the necessary server components are installed on the remotely hosted DMS 60'. In some implementations, a business-to-business (B2B) virtual private network (VPN) can be created between the remotely hosted DMS 60' and the network of the facility 40 or facility system 18, 20. In this manner, the facility 40 and/or facility system 18, 20 forgoes the purchase and/or maintenance of another physical server, or DMS 60. Further, the up-time and the status of availability of the DMS 60' are easier to manage on the part of a dedicated third-party. The DMS' access to the network can be attended to by the third-party, as opposed to burdening the facility 40, or the facility systems 18, 20. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

The DMS 60, 60' synchronizes and transfers data between the remote device 12, or multiple remote devices 12, and the information system 42, or multiple information systems 42. More specifically, the DMS 60, 60' processes and prepares the patient data and/or patient information for transfer to and presentation on the remote device 12, or multiple remote devices 12, from the information system 42. The DMS 60, 60' also processes and prepares ancillary information for transfer to and storage in the information system 42 from the remote device 12, or multiple remote devices 12 for potential presentation at a corresponding computer device 44. Exemplar DMSs can include, but are not limited to, the AirStrip Server provided by AirStrip Technologies, LLC, which AirStrip Server includes AirStrip Server Components installed therein.

Figure 3:
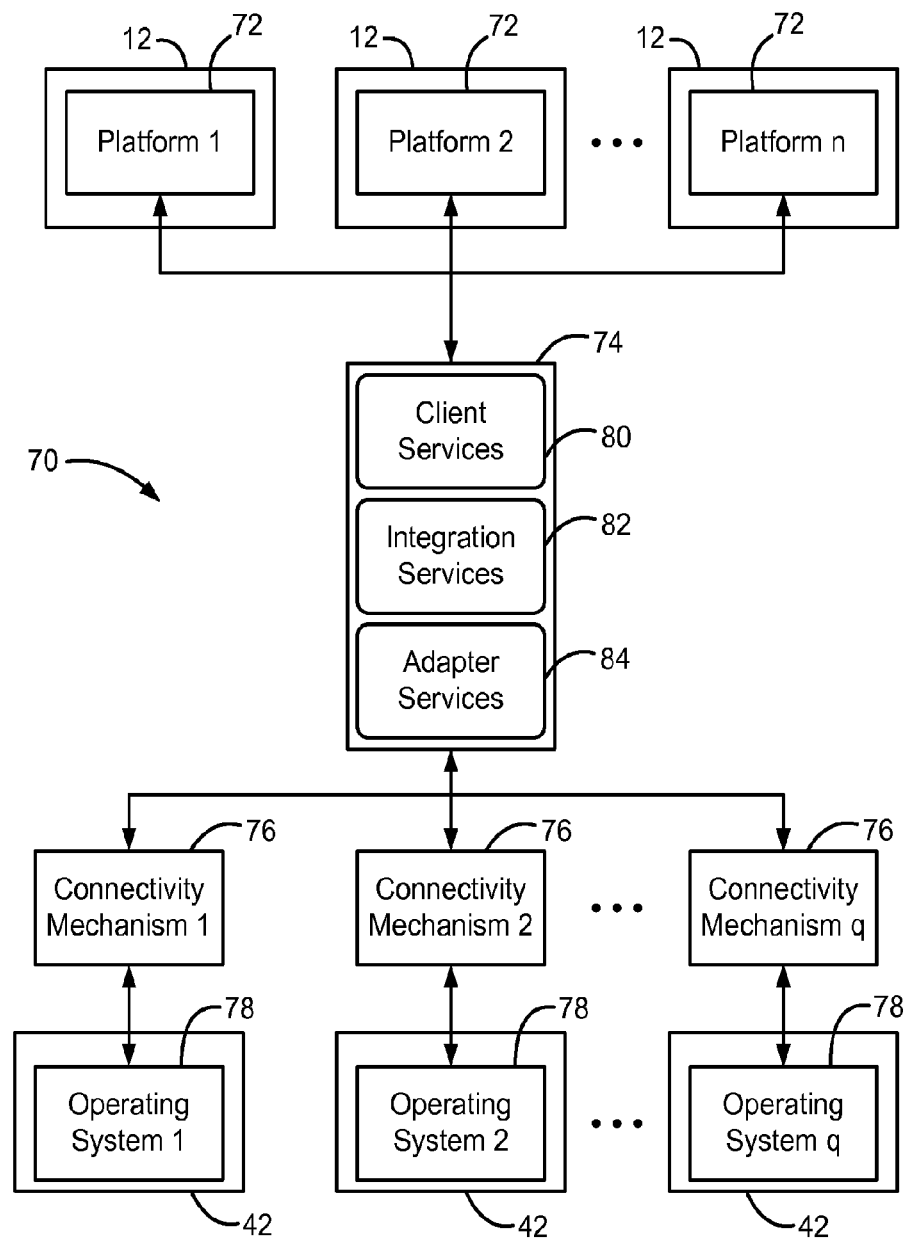
FIG. 3 is a functional block diagram of components that can be used to implement the present disclosure.
Figure 4:
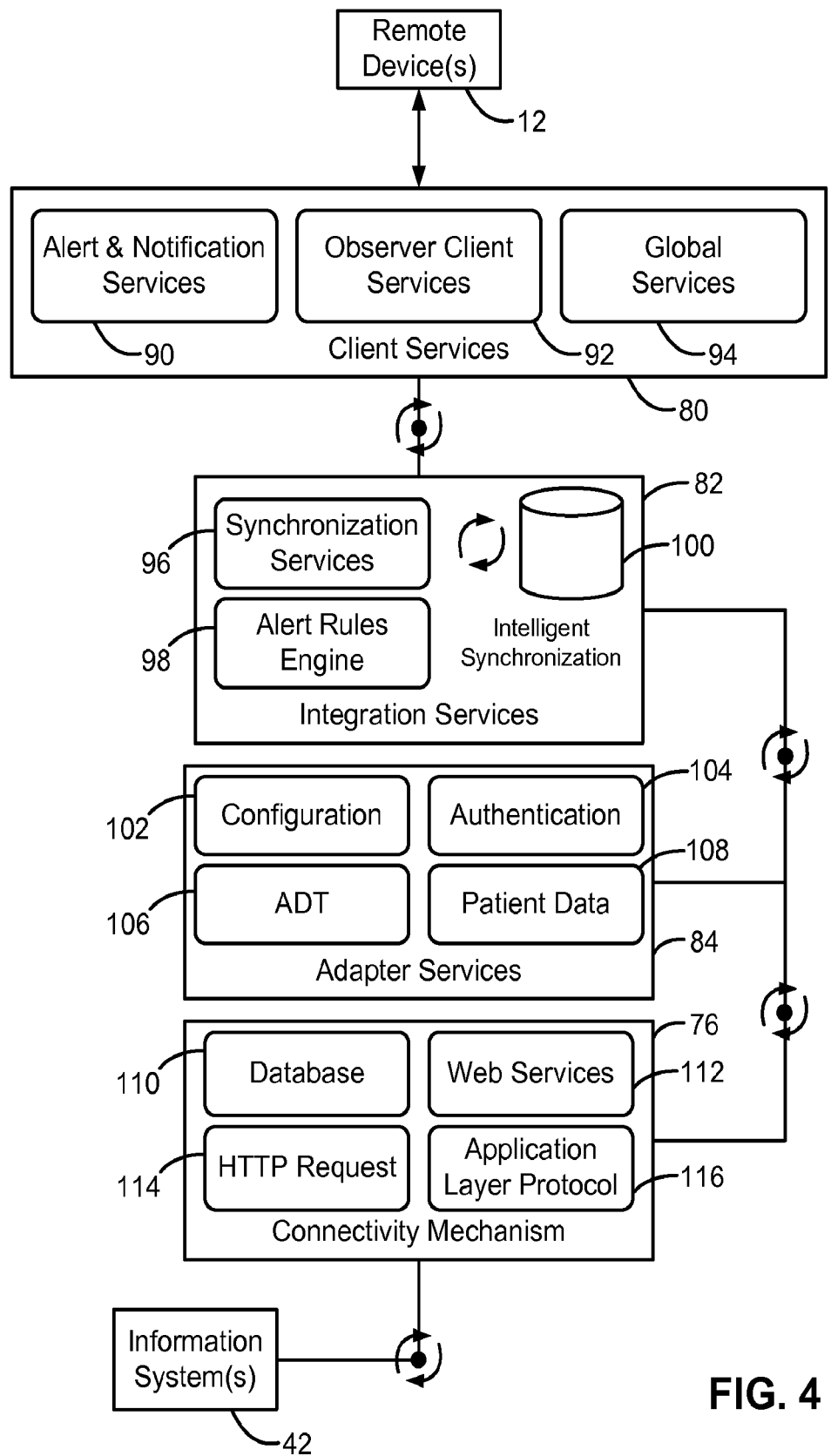
FIG. 4 is a more detailed view of the functional block diagram of FIG. 3.

Referring now to FIGS. 3 and 4, an exemplar software component, or module structure 70 to implement the features of the present disclosure will be described in detail. The exemplar structure enables patient data and patient information to be communicated to/from, and to be synchronized between the information system 42 and the remote device 12, regardless of the operating system, or platform, operating on the remote device 12. Exemplar platforms include, but are not limited to, RIM Blackberry, Apple iPhone, MS Pocket PC 2003, Win Mobile 5.x (Pocket PC, Smartphone), Win Mobile 6.x (standard, professional) and/or any platforms to be developed (e.g., Google Android, and Palm PRE).

FIG. 3 illustrates an overview of the exemplar module structure 70, which includes a platform 72, or operating system, of the remote device 12, intermediary components 74, a connectivity mechanism 76, and an operating system 78 of the information system 42. In this arrangement, the remote device 12 is a client that executes a client application thereon. The intermediary components 74 are resident on the DMS 60, 60', and include a client services module 80, an integration services module 82, and an adapter services module 84. The DMS 60, 60' functions as an intermediary between the platform 72 resident on the remote device 12 and the operating system 78 of the information system 42. A plurality of platforms 72 is illustrated to exemplify the ability of the DMS 60, 60' to transfer data to and from any platform 72 operating on the remote device 12. The connectivity mechanism 76 enables communication between the DMS 60, 60' and a particular information system 42. A plurality of connectivity mechanisms 76 and corresponding operating systems 78 is illustrated to exemplify the ability of the DMS 60, 60' to transfer data to and from any operating system 78 on the information system 42.

In the exemplar structure illustrated in FIG. 4, the client services module 80 includes an alert and notification services module 90, an observer client services module 92, and a global services module 94. The integration services module 82 includes a synchronization services module 96, and an alert engines rule 98. The synchronization services module 96 can communicate with a synchronization database 100 to provide so-called intelligent synchronization. The adapter services module 84 includes a configuration module 102, an authentication module 104, an admission, discharge and transfer (ADT) module 106, and a patient data module 108.

The alert and notification services module 90 sends alerts and/or notifications to the remote device 12, as discussed in further detail below. The observer client services module 92 facilitates communication between client applications, running on the remote device 12, and backend server components that provide access to application data. The observer client services module 92 transmits data through a formatted request, and receives data in a proprietary data format. An exemplar data format includes, but is not limited to, JavaScript Object Notation (JSON), which is a lightweight computer data interchange format that provides a text-based, human-readable format for representing simple data structures and associative arrays, called objects). The global services module 94 communicates with the client running on the remote device 12 and performs registration and client application configuration settings. Client application settings can be customized by the user of the remote device 12, and the facility 40 and/or facility systems 18, 20, for which the remote device 12 is configured to receive data.

The integration services module 82 is responsible for routing requests that are received from the observer client services module 92 to retrieve and package requested data, and to send a corresponding response. More specifically, the integration services module 82 requests data from the adapter services module 84, or from the synchronization database 100 depending on how the particular DMS 60, 60' is configured. If the DMS 60, 60' is configured to use a vendor adapter, the request goes directly to the adapter services module 84 to retrieve the data. If the DMS 60, 60' is configured for synchronization, then the data is retrieved from the synchronization database 100. The synchronization services module 96 communicates with the adapter services module 84 to maintain the synchronization database 100 current using intelligent synchronization.

Intelligent synchronization is synchronization executed based on variable configuration parameters, which enable the possibility of only some of the patient data and/or patient information to be synchronized as opposed to all of the available data being continuously synchronized. By using custom business rule logic to intelligently determine which patient data and/or information should be synchronized, and which patient data and/or information should be synchronized, the DMS 60, 60' functions more efficiently and can service an increased number of clients and configurations. By way of non-limiting example, prior to a user logging on to the DMS 60, 60' via the remote device 12, no specific patient data and/or information is synchronized. Instead, only a patient census list and specific data elements corresponding to particular patients 50 are synchronized between the DMS 60, 60' and the information system(s) 42. Once the user logs on, and selects a particular patient 50 to review, the synchronization services begin synching all of the available patient data and/or information for that particular patient 50. Consequently, subsequent reviews of the particular patient 50 are much faster, because the patient data and/or information has been synchronized.

The adapter services module 84 is the mechanism that retrieves data from the information system 42, through the connectivity mechanism module 76, and that structures the data for the DMS 60, 60'. The data is formatted and rules are applied for the specific DMS 60, 60', for which the adapter has been written, regardless of whether the data is directly requested for a client through the integration services module 82, or is retrieved through the synchronization services module 96. The configuration module 102 captures configuration settings used by the information system(s) 42. The configuration module 102 can use already existing configuration information so that it does not have to be replicated in the DMS 60, 60'. By way of non-limiting example, all of the patient beds of a particular facility 40, and to which unit(s) they belong are typically stored in the information system(s) 42. The configuration module 102 reduces, or obviates manual effort in entering the configuration information. The configuration module 102 can also prevent problems from occurring when a configuration change is made in the information system(s) 42, but a system administrator forgets to make the change in the DMS 60, 60'.

The authentication module 104 handles the authentication needs of the DMS 60, 60', which can include, but are not limited to active directory authentication, vendor authentication, device ID restrictions, device phone number restrictions, and any combination thereof. Each facility system 18, 20 and/or facility 40 is configured to authenticate using any combination of such authentication mechanisms. Device ID restriction is the ability for an authentication service to look at a pre-configured list of device ID's, associated with respective remote devices 12, that are authorized to connect to the facility system 18, 20 and/or facility 40, and only authorizes call from software client that originate with that device ID (i.e., from the particular remote device 12). The device phone number restriction restricts access to remote devices 12 that have a phone number that has been pre-configured in the authentication system.

The ADT module 106 enables the use of existing ADT interfaces within the facility system 18, 20 and/or facility 40 to obtain patient admission, discharge and transfer information in order to always know which patient is associated to which bed and/or unit. The patient data module 108 provides all waveform and non-waveform patient data and/or information from the information system(s) 42 to the DMS 60, 60'. The patient data module 108 can also provide all waveform and non-waveform acquired from a data acquisition system such as the AirStrip data collector or an independent data collecting system including but not limited to Capsule Technologies' Data Captor system. This includes, but is not limited to, all nursing charting information as well as any automated means of data collection used by the information system(s) 42.

In the exemplar structure illustrated in FIG. 4, each connectivity mechanism module 76 includes a database module 110, a web services module 112, a request module 114, and an application layer protocol module 116. By way of non-limiting example, the request module 114 can manage HTTP requests, and/or the application layer protocol can include the health level seven (HL7) application layer protocol. The connectivity mechanism module 76 enables the DMS 60, 60' to connect to and communicate with the particular information system 42. In some implementations, the connectivity mechanism module 76 can include application protocol interfaces (APIs), through which it communicates with the information system 42. In other implementations, the connectivity mechanism module 76 can directly access the information system 42.

As discussed at the outset, the present disclosure provides a healthcare provider, or user of the remote device 12, with secure, remote access to patient data and/or patient information. As used herein, the term patient data refers to physiological data that can be obtained from the patient monitoring device(s), and/or physiological patient data that is input into the information system 42 by a local healthcare provider (e.g., a nurse, or physician). The term patient information refers to information corresponding to a particular patient that is input into the information system 42 by the local healthcare provider. Exemplar patient information can include, but is not limited to, the patient's name, the name of the doctor(s) assigned to the patient, the nurse(s) assigned to the patient, a facility identification, a patient bed identification, a summary of key patient data, and/or chart annotations. In the exemplar case of a maternity patient, the key patient data can include, but is not limited to, delivery progress information such as cervical exam status, membrane status, gravida, para, epidural status, and/or whether the patient is attempting a vaginal birth after cesarean (VBAC).

The patient data and/or patient information provided to the remotely located user can be provided in real-time data, and/or as historical data and information. The patient data and/or patient information is communicated between the remote device 12 and the DMS 60, 60' using a secure connection that is established over the network 16. A secure log-in, or sign-on process is provided, which is preferably compliant with the provisions of the Health Insurance Portability and Accountability Act (HIPAA). The secure sign-on authenticates the identity of the user of the remote device 12 based on a unique user ID and password combination. Both the user ID and the password must be correct in order to establish the secure communication between the remote device 12 and the DMS 60, 60'. Implementations of sign-on and authentication processes are described in further detail below.

A census, or patient list is provided to the remote device 12, which captures a variety of the information and/or data described herein that is associated with each of one or more monitored patients 50. Strip charting is also provided, in which patient data and/or information can be presented to the user in graphical form. In the exemplar case of a maternity patient, a fetal strip and maternal contraction information can be provided for a particular patient 50. More specifically, the particular patient 50 is selected from the patient list, and the patient information and/or data is subsequently presented. The presented information and/or data can include a fetal strip and maternal contraction waveform, the patient name, the hospital name, the patient room and/or bed number, and the date and time. The strip charting can provide a real-time view of the patient data, as well as a historical view of the patient data. More specifically, the waveform display can be updated in real-time, such that the user of the remote device 12 observes the patient data as it occurs and/or is recorded. The user can scroll through the waveform display, to view historical patient data, as described in further detail below.

Several navigation features can be provided that enable the user to manipulate a view of the waveform display. In some implementations, the user can zoom in/out of the displayed image. In this manner, the user can view very specific waveform information, and/or other waveform micro-characteristics by zooming in, for example, and/or can view patterns or other waveform macro-characteristics by zooming out, for example. In some implementations, the user can scroll forward or backward through the waveform display. In this manner, the user can view historical patient data.

A patient data display can also be provided. In some implementations, the patient data display can overlay the strip charting described herein. In other implementation, the patient data display can be provided as an overlay, and/or as a separate display. The patient data display can include, but is not limited to, the patient's name, age, fetal gestation, gravida, parity, cervical exam information, and physician name.

Implementations of the present disclosure can be realized on any one of a number of operating systems, or platforms 72 associated with the particular remote device 12. As discussed above with reference to FIGS. 3 and 4, exemplar platforms include, but are not limited to, RIM Blackberry, Apple iPhone, MS Pocket PC 2003, Win Mobile 5.x (Pocket PC, Smartphone), Win Mobile 6.x (standard, professional) and/or any platforms to be developed (e.g., Google Android, and Palm PRE). Referring now to FIGS. 5A-5K exemplar implementations of the present disclosure will be described with reference to screen-shots of an exemplar remote device 12. The remote device 12 of the instant example includes a mobile device, such as a cellular telephone, or smartphone, that includes an exemplar platform (e.g., Apple iPhone). It is appreciated, however, that implementations of the present disclosure can be executed on any type of remote device 12, and/or using any type of platform 72 that is supported by the remote device 12. It is appreciated that the screen-shots illustrated and described herein are merely exemplar in nature, and are not exhaustive of the functionality and features provided in implementations of the present disclosure.

Figures 5A, 5B:
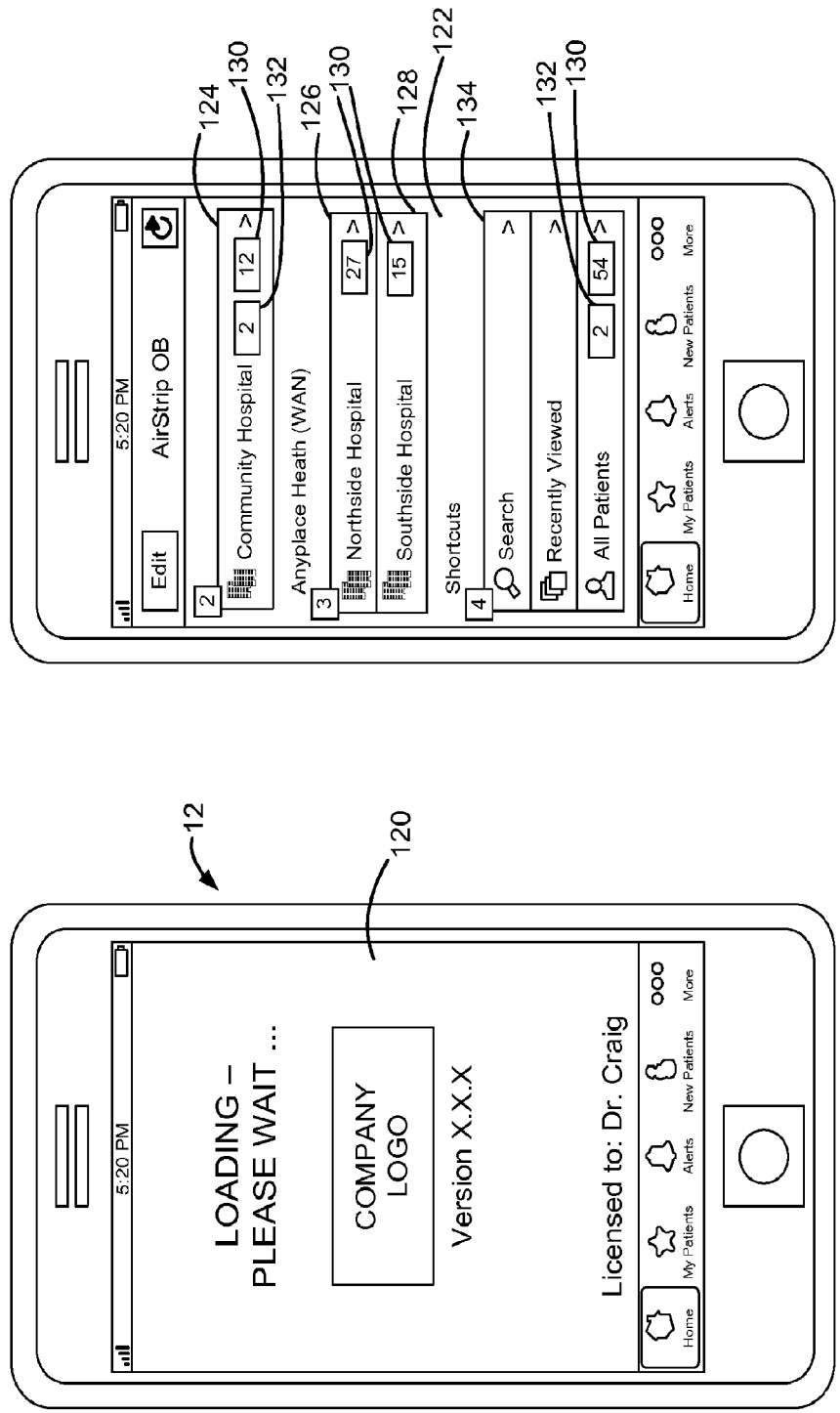

FIG. 5A illustrates an exemplar screen-shot of a loading screen 120 that is initiated after the user inputs a user ID and password combination. If the user ID and password combination is authenticated, secure communication between the remote device 12 and the DMS 60, 60' is established, and the remote device 12 retrieves patient data and/or information from the DMS 60, 60'. In some implementations, the user may be associated with more than one facility system 18, 20, with each facility system 18, 20 including its own DMS 60 (see, for example, FIG. 1). In such cases, secure communication between each of the DMS 60 and the remote device 12 is established upon the confirmation of the user ID and password combination, as explained in further detail herein.

FIG. 5B illustrates an exemplar screen-shot of a facility summary display 122 that provides a summary of the facility system(s), and/or particular facility, or facilities, with which the user is associated. The facility summary display 122 includes a plurality of selectable icons. The exemplar illustration of FIG. 5B provides a facility icon 124 (e.g., "Community Hospital"), and a facility system (e.g., "Anyplace Health (WAN)") that includes two facility icons 126, 128 associated therewith (e.g., "Northside Hospital," and "Southside Hospital"). The facility (e.g., "Community Hospital") can be a stand-alone facility that is not associated with a facility system (e.g., "Anyplace Health (WAN)"). In this case, the facility can be described as "non-WAN", because it is not networked with other facilities, and/or a facility system. The facility system can be described as "WAN," because it is a facility system that includes a plurality of inter-communicating facilities associated therewith.

With particular reference to the facility system icons 126, 128, attributes can be provided. Exemplar attributes can include, but are not limited to, patient counts. A first patient count 130 provides the total number of patients at the facility, for which the particular user is responsible. For example, if the user is a physician, the first patient count 130 illustrates the total number of patients that are under the care of that particular physician. In the exemplar illustration of FIG. 5B, the total number of patients associated with the user at "Community Hospital" is twelve, the total number of patients associated with the user at "Northside Hospital" is twenty seven, and the total number of patients associated with the user at "Southside Hospital" is fifteen. A second patient count 132 can be provided, which displays a specific patient count. The specific patient count can include the number of patients deemed to be new patients. In the exemplar illustration of FIG. 5B, a specific patient count of two is associated with the "Community Hospital." This can indicate, for example, that of the twelve patients at "Community Hospital," two are deemed to be new patients.

The exemplar facility summary display of FIG. 5B further includes a shortcut menu 134 that provides links to exemplar functions, and/or other displays. Although the illustrated exemplar links include "Search," "Recently Viewed," and "All Patients," it is contemplated that the shortcut menu 134 can be customized by the user to provide any available links that the user desires. By selecting "Search," a search screen is provided, in which the user can input search terms to search for patients, facilities, facility systems, and the like. By selecting "Recently Viewed," a display screen is provided, in which a number of patients, whose patient data has been recently viewed by the user using the remote device are listed. By way of non-limiting example, the list of patients can be determined by a fixed count (e.g., the last X number of patients that the user has viewed), and/or can be determined by a time (e.g., the patients viewed by the user over the last X day(s)). By selecting "All Patients," a display screen is provided, which lists all of the patients that are assigned to the specific user, regardless of facility or facility system. The "All Patients" link can also include a total patient count 130, and a specific patient count 132. In this case, the total patient count 130 within the shortcut menu 134 indicates the number of patients that are under the care of that particular user, regardless of the facility, and the specific patient count 132 can indicate the number of new patients of the total.

The user can navigate from the facility summary display 122 by selecting any one of the icons. An icon can be selected in any one of a number of manners that is supported by the particular platform. By way of non-limiting examples, an icon can be selected by touching the screen with a digit (i.e., finger), a stylus, and/or other pointing device, as well as with a digital cursor, and/or a keypad.

Figures 5C, 5D:
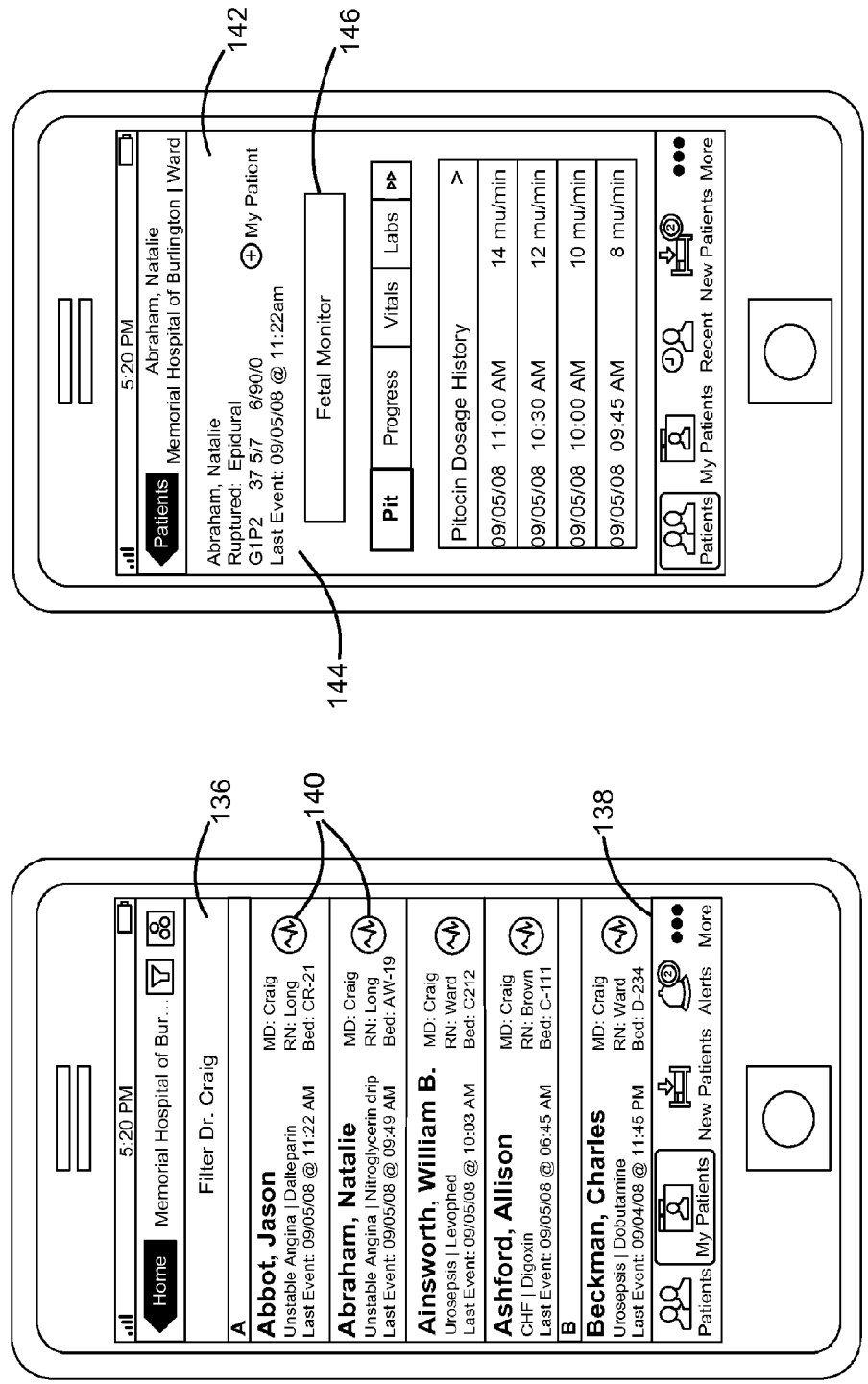

FIG. 5C illustrates an exemplar screen-shot of a patient summary display 136 that provides a summary of the patients associated with a particular facility (e.g., "Memorial Hospital" in the exemplar illustration of FIG. 5C). The summary can include patient data and/or information. In the exemplar illustration of FIG. 5C, the summary information includes the patient's name, the attending nurse's name, the responsible physician's name, the patient's bed number, the date and time of the most recent, or last, medical event, a condition (e.g., "Unstable Angina," "Urosepsis," and/or "Congestive Heart Failure (CHF)"), as well as a particular medication prescribed to the patient. A particular summary type can be selected from a menu 138. In the exemplar illustration of FIG. 5C, the menu 138 is provided as a touch screen menu, and includes a plurality of selectable options. It is contemplated, however, that the menu 138 can be provided in any one of a number of manners including, but not limited to, a drop-down menu. The illustrated, exemplar options of the menu 138 include "Patients," "My Patients," "New Patients," "Alerts," as well as the option "More" to display additional options. In the exemplar illustration of FIG. 5C, the patient summary display 136 lists the patients associated with the particular user (e.g., "Dr. Craig") at the particular facility (e.g., "Memorial Hospital"). By selecting "Patients," all of the patients at the particular facility can be displayed. By selecting "New Patients," only those patients that are deemed to be new patients are displayed. By selecting "Alerts," patients having a corresponding alert status, discussed in further detail herein, are displayed. A selectable chart 140 icon can also be provided for each patient listed. By selecting the chart icon, one or more graphical strip charts of patient data and/or patient information can be displayed, as discussed in further detail below.

Figure 5F:
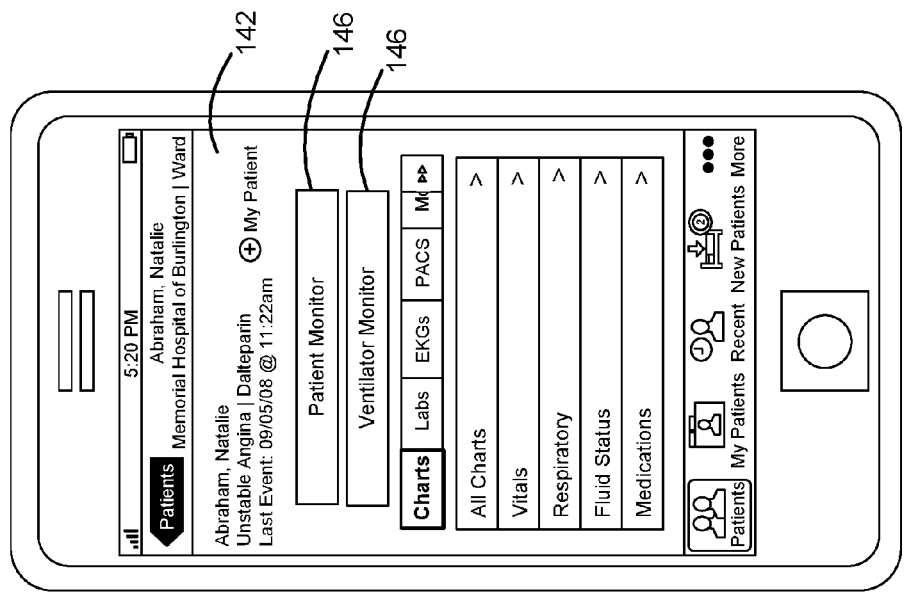
Figure 5E:
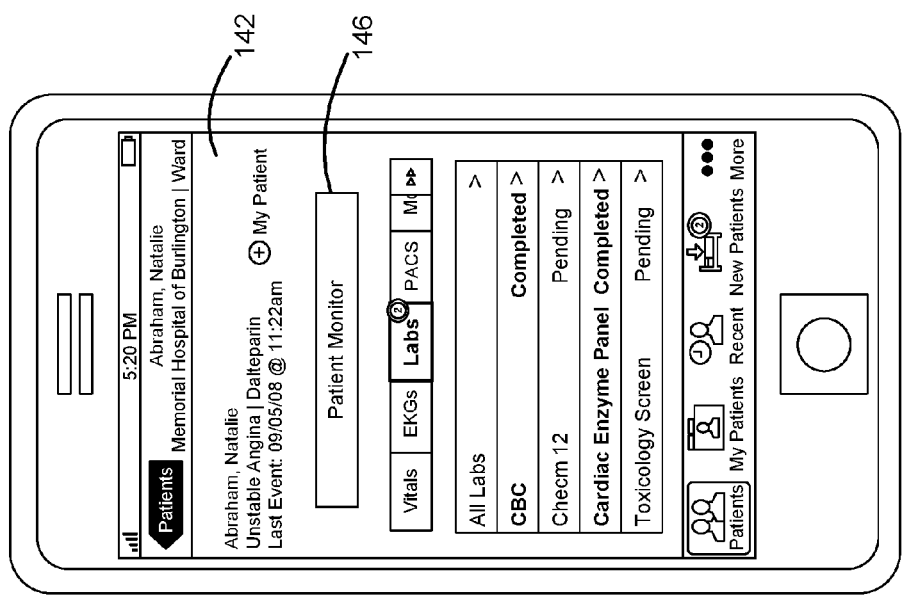

By selecting a particular patient from the patient summary display 136, a specific patient summary display 142 is provided. FIG. 5D illustrates an exemplar specific patient summary display 142 for the patient "Abraham, Natalie" selected from the patient summary display 136. The specific patient summary display 142 can provide a variety of summarized patient data and/or information 144. The specific patient summary 142 further includes selectable icons for drilling down to more specific patient information. For example, a monitor icon 146 can be provided, which enables the user to view graphical strip charts of patient data and/or patient information, as discussed in further detail below. In the exemplar context of a maternity patient, the selectable icon is provided as a "Fetal Monitor" icon. Other patient data and/or information can be viewed on the specific patient summary display. In the exemplar illustration of FIG. 5D, a selectable menu is provided, through which the user can select particular summary data and/or information to view. The exemplar options illustrated in FIG. 5D include, but are not limited to, a medication dosage history, a progress history, vitals, and laboratory results. FIGS. 5E and 5F illustrate other, exemplar specific patient summary displays 142 that include other monitor icons 146 (e.g., "Patient Monitor," and "Ventilator Monitor"), as well as other available summary data and/or information (e.g., electrocardiograms (ECGs or EKGs), charts, and PACS).

Referring now to FIG. 5G, an exemplar screen-shot of a patient vital display 150. The patient vital display 150 can provide patient data values and/or can display the patient data graphical form (e.g., as a strip). In the exemplar illustration of FIG. 5G, values of patient vitals are provided, and the patient vitals are shown in graphical form. The exemplar patient vitals include, but are not limited to, heart rate, blood pressure, oxygen saturation, end-tidal $CO_2$, Swan tracing, Arterial Line Tracing, Central Venous Pressure, EKG/ECG, Ventilator waveforms and body temperature. The patient vitals can be provided as a static display, can be displayed in real-time (i.e., updated as measurements are taken by the patient monitoring device(s)), and/or can be played back (i.e., playback stored patient data to provide a historical display).

FIG. 5H illustrates an exemplar screen-shot of a patient display 152, which display summary strips 154 associated with particular patient data. In the exemplar context of a maternity patient, the display summary strips 154 include, but are not limited to a fetal strip, labor curve, and blood pressure. A note summary 156 can also be provided. By selecting one of the display summary strips 154, the corresponding strip can be displayed in more detail, as described below with respect to FIGS. 5I and 5J. By selecting the note summary 156, nursing notes and information pertinent to the particular patient can be displayed to provide specific detail.

The exemplar implementations of FIGS. 5I and 5J provide a fetal strip 158. It is appreciated, however, that implementations of the present disclosure can display any type of pertinent data strip including, but not limited to, a fetal strip, a labor curve, blood pressure, heart rate, oxygen saturation, end-tidal $CO_2$, Swan tracing, Arterial Line Tracing, Central Venous Pressure, EKG/ECG, Ventilator waveforms and/or body temperature. The exemplar illustration of FIG. 5I provides the fetal strip in a portrait layout, and the exemplar illustration of FIG. 5J provides the fetal strip in a landscape layout. The landscape layout enables the user to either view a greater amount of patient data over a longer time period, or view the patient data in expanded detail across the same time period.

Upon selecting the particular strip for display, a request is made from the remote device 12 to the corresponding information system 42 to transmit the patient data and/or information for the particular patient. The patient data and/or information is provided to the remote device 12, with the remote device 12 buffering the patient data and/or information to provide real-time viewing thereof. Basic real-time viewing of the patient data is provided on a background grid with a timing mark shown and patient information being provided. In implementations of the present disclosure, the patient data trace moves from right to left across the display.

In implementations of the present disclosure, provide zoom in and out functionality. In each case, the user can take advantage of viewing a trend (e.g., zoom out), or a specific data segment (e.g., zoom in) to facilitate a judgment with regard to the condition of the patient. Implementations of the present disclosure also provide variable speed scroll functionality of the data strip. More specifically, the user of the remote device 12 can be presented with a bi-directional, multilevel selection bar, and/or virtual controls that regulate the direction and the scrolling speed of the data strip. In this manner, the user can customize viewing of the patient data to personal preferences, or to the specific situations that dictate review of the patient data. For example, the user may quickly scroll through the data strip to a point, at which a particular anomaly occurred, and can more slowly scroll the data strip around that point to study the patient data in further detail.

Figures 6A, 6B:
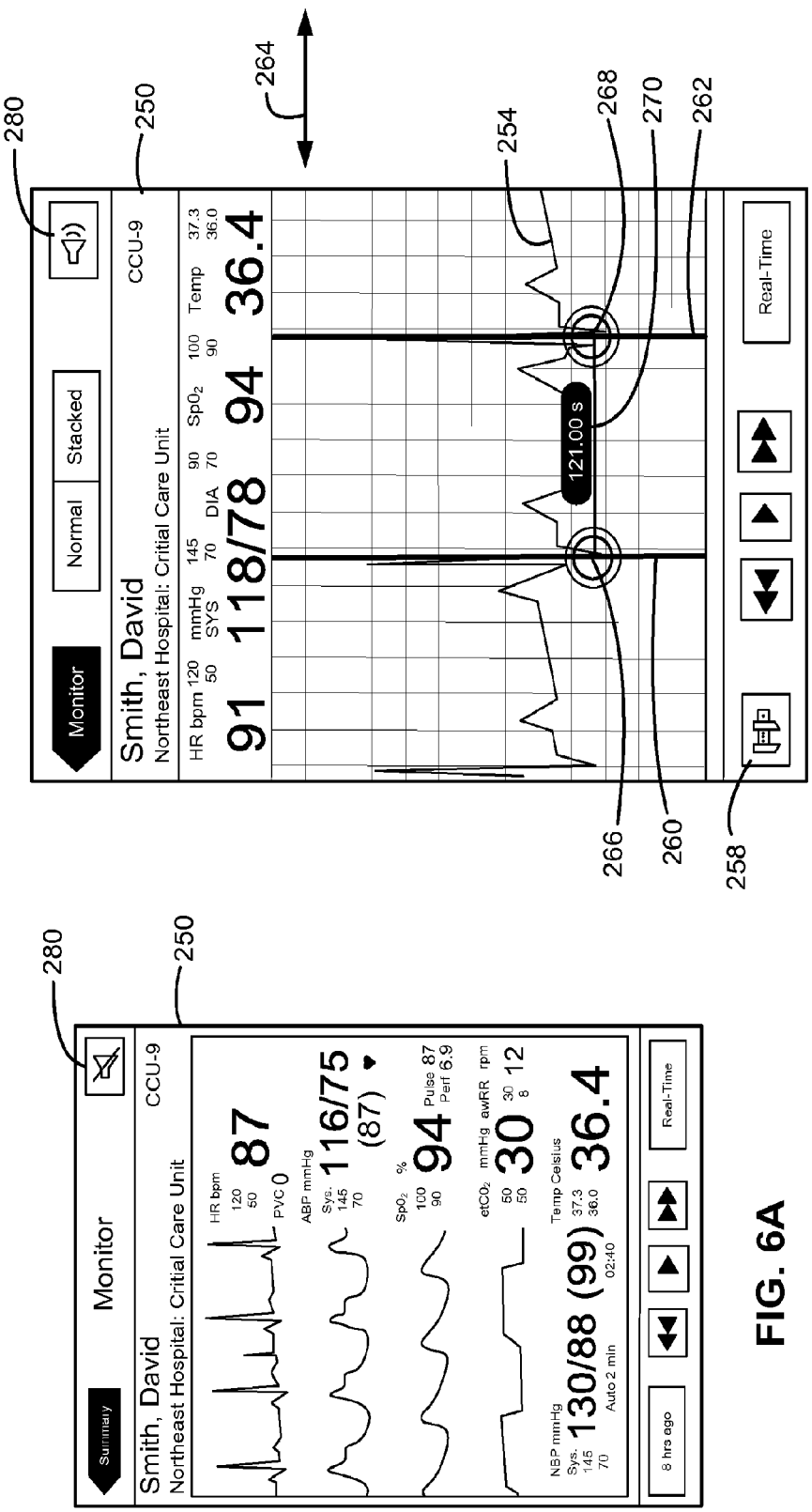
FIGS. 6A-6C provide exemplar screenshots illustrating features in accordance with the present disclosure.
Figure 6C:
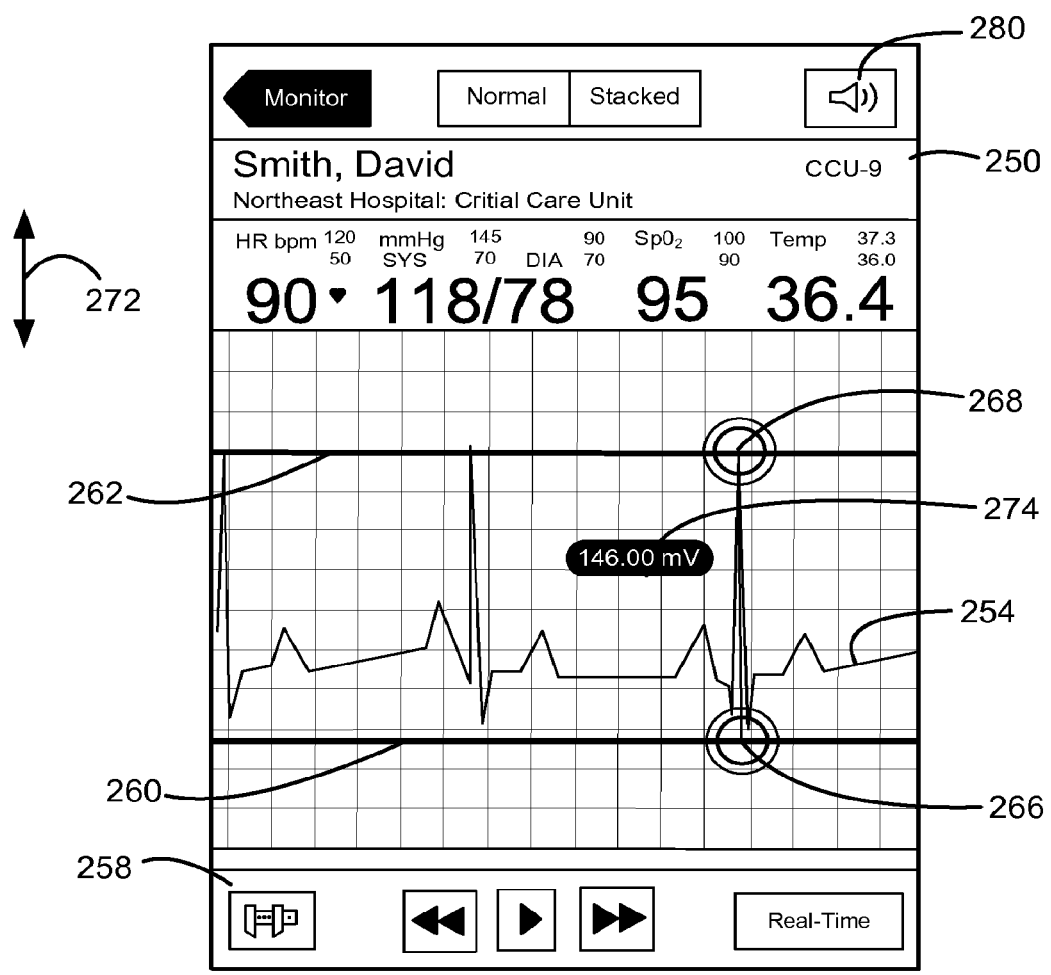
Figure 7:
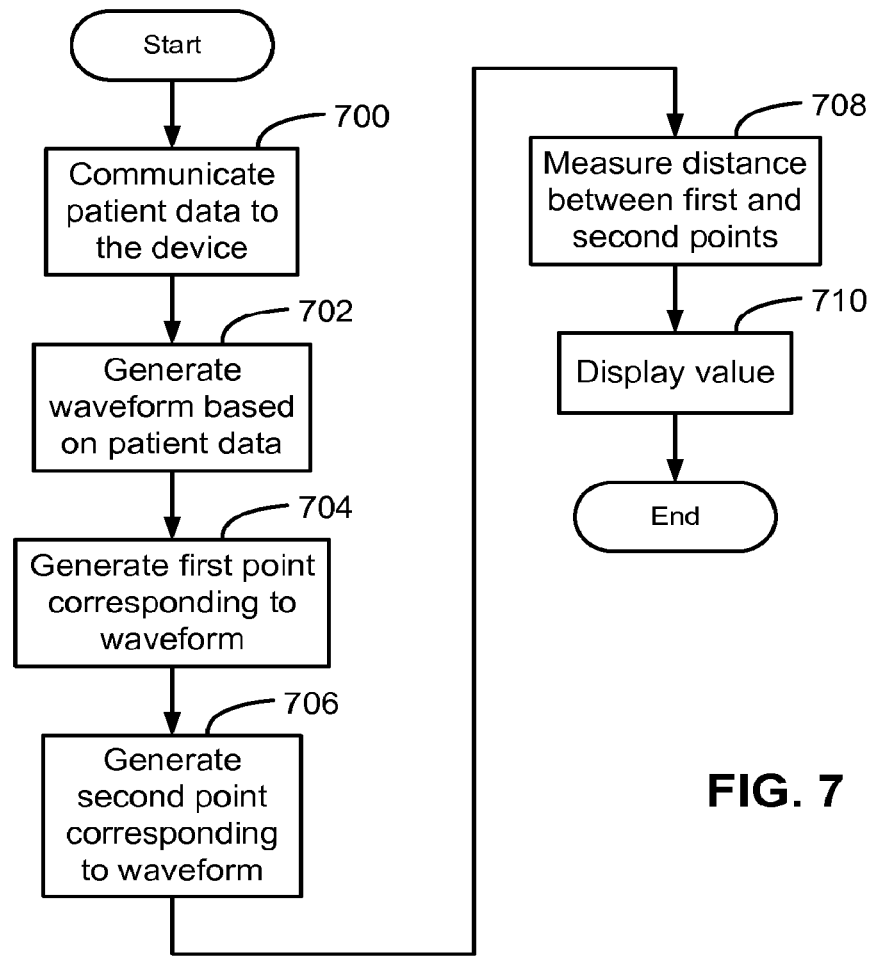
FIG. 7 is a flowchart illustrating exemplar steps that can be executed to provide waveform measuring in accordance with the present disclosure.

Referring now to FIGS. 6A-7, touch-measurement of waveforms displayed on the remote device 12 will be described. With particular reference to FIG. 6A, an exemplar screen-shot of a patient vital display 250 is illustrated, and is similar to that shown in FIG. 5G. The patient vital display 250 can provide patient data values and/or can display the patient data graphical form (e.g., as a strip, or waveform). In the exemplar illustration of FIG. 6A, values of patient vitals are provided, and the patient vitals are shown in graphical form. The exemplar patient vitals include, but are not limited to, heart rate, blood pressure, oxygen saturation, end-tidal $CO_2$, Swan tracing, Arterial Line Tracing, Central Venous Pressure, EKG/ECG, Ventilator waveforms and body temperature. The patient vitals can be provided as a static display, can be displayed in real-time (i.e., updated as measurements are taken by the patient monitoring device(s)), and/or can be played back (i.e., playback stored patient data to provide a historical display).

The user of the remote device 12 can select a particular waveform to be presented in detail on the display of the device 12. For example, the display can be provided as a touch-screen display, in which contact with the display can be registered as input to the device 12 to regulate operation thereof. Such contact can be achieved by direct contact by the user (e.g., using fingertips), and/or contact using a stylus. If the user selects the heart rate waveform in FIG. 6A, the exemplar screen-shots of FIGS. 6B and 6C can be displayed. With particular reference to FIG. 6A, the heart rate waveform 252 can be shown in real-time as the underlying patient data is received by the remote device. For example, the user can select a "Real Time" display button to view the waveform 252 in real-time. Playback buttons 256 are also included to provide a historical review of the waveform 252, and to pause the real-time updating of the waveform 252.

A measurement button 258 is provided to enable the user to measure select waveform features. By selecting the measurement button, a digital caliper is generated on the display and includes a first caliper line, or jaw 260, and a second caliper line, or jaw 262. If the user would like to make a waveform measurement along a horizontal direction 264 (e.g., along a time axis) the caliper lines 260, 262 are aligned perpendicular to the horizontal direction 264, and are movable therealong (see FIG. 6B). Points 266, 268 can be generated on the caliper lines 260, 262, respectively, corresponding to where the first and second caliper lines 260, 262 intersect the waveform 252. A measurement value 270 is automatically generated based on the positions of the caliper lines 260, 262 along the horizontal direction 264. The respective positions of the caliper lines 260, 262 can be manipulated by touching the display and dragging a selected caliper line 260, 262 along the horizontal direction 264. As the selected caliper line 260, 262 moves, the measurement value 270 can be automatically updated in real-time as the movement occurs. In the exemplar screen-shot of FIG. 6B, the measurement value 270 corresponds to a time measurement between peaks of the waveform 252.

If the user would like to make a waveform measurement in the vertical direction 272 (i.e., along a voltage axis) the caliper lines 260, 262 are aligned perpendicular to the vertical direction 272, and are movable therealong (see FIG. 6C). Points 266, 268 are generated on the caliper lines 260, 262, respectively, corresponding to where the first and second caliper lines 260, 262 intersect the waveform 252. A measurement value 274 is automatically generated based on the positions of the caliper lines 260, 262 along the vertical direction 272. The respective positions of the caliper lines 260, 262 can be manipulated by touching the display and dragging a selected caliper line 260, 262 along the vertical direction 272. As the selected caliper line 260, 262 moves, the measurement value 274 can be automatically updated in real-time as the movement occurs. In the exemplar screen-shot of FIG. 6C, the measurement value 274 corresponds to a voltage measurement between a peak and a trough of the waveform 252.

Referring now to FIG. 7, a flowchart illustrates exemplar steps that can be executed to provide waveform measurement on the display of the device 12. In step 700, patient data is communicated to a device, which is remote from a source of the patient data. In step 702, a waveform is generated on a touch-screen display of the device. A first point is generated corresponding to the waveform based on contact with the touch-screen display in step 704, and a second point is generated corresponding to the waveform based on contact with the touch-screen display in step 706. In step 708, a distance between the first point and the second point is automatically measured along the axis upon generation of the second point. In step 710, a value corresponding to the distance is displayed on the touch-screen display. The value can include one of a time value and a voltage value. As discussed above at least one of the first point and the second point can be moved along the axis, and the value updated in real-time based on movement of the at least one of the first point and the second point along the axis. The value can be stored in a memory of the device, and/or the value can be communicated to a patient information system located at a facility.

As seen in each of FIGS. 6A-6C, an audio button 280 can be provided in the display. The audio button 280 can be selected to turn auditory features of the device 12 ON or OFF. The auditory features can correspond to auditory features that are available from the patient monitoring devices 46 that directly monitor the patient 50 at a facility 40. More specifically, the audio features of the device 12 simulate those of the patient monitoring devices 46. In this manner, the user of the device 12 can audibly monitor the patient from a remote location, as if the user were audibly monitoring the patient directly at the facility 40. The auditory features can be emitted from the device 12 using a speaker.

The auditory features can be provided for each of the exemplar waveforms described herein. By way of non-limiting example, auditory features can be provided for pulse oximetry and/or heart rate. With particular reference to 6A, the user of the device 12 is presented with waveforms for particular patient vital signs, which waveforms may be updated in real-time based on received patient data. As certain features (e.g., spike, peak, trough, flat line) occur for a particular waveform, a sound is generated corresponding to the occurrence of the features. In the case of a heart rate waveform, a sound can be generated based on the waveform spikes, or peaks that correspond to a patient's heartbeat. In this manner, the sound is periodically repeated and an audible cadence is presented to the user, enabling the user to audibly monitor the patient's heart rate. In some cases, such as when the waveform is flat, or featureless, a persistent sound can be generated. Such a case can occur, for example, when the patient's heart stops beating and is in a so-called "flat line" condition. The sound can be stored as an audio file, or multiple audio files in memory 26 of the device 12, and can correspond to a particular audio file format (e.g., way, mp3, m4p).

Figure 8:
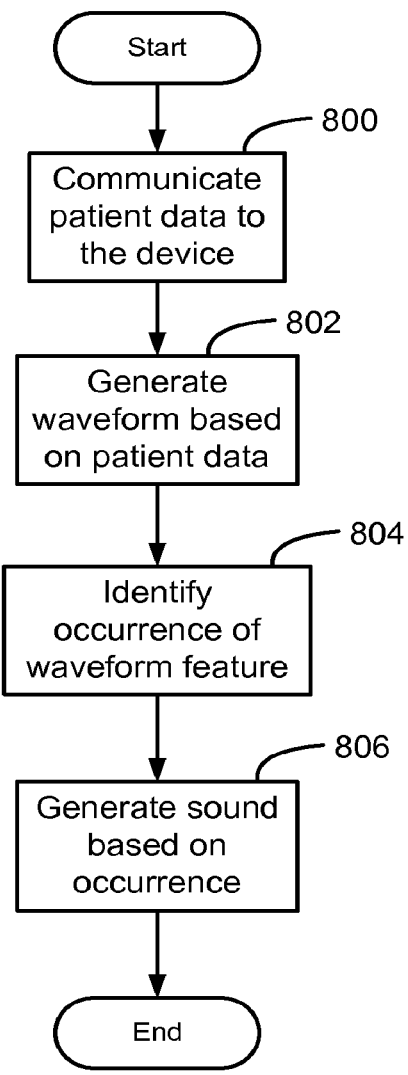
FIG. 8 is a flowchart illustrating exemplar steps that can be executed to provide audible monitoring of patient information in accordance with the present disclosure.

Referring now to FIG. 8, a flowchart illustrates exemplar steps that can be executed to provide the above-described auditory features. In step 800, patient data is communicated to the device, the device being remote from a source of the patient data. In step 802, a waveform is generated on a display of the device based on the patient data. In some cases, the waveform can correspond to one of a heart rate, a blood pressure, an oxygen saturation, and an end-tidal $CO_2$. In some cases, the waveform feature can include one or more of a spike, a peak, a trough and a flat line. An occurrence of a waveform feature is identified in step 804, and a sound is generated based on the occurrence of the waveform feature in step 806. The sound can be repetitively generated in response to periodic occurrences of the waveform feature. The sound can be a persistent sound. In some cases, an audio file can be stored in memory of the device, and can be retrieved based on generating the waveform, the sound being generated based on the audio file. In some cases, a plurality of audio files can be stored in memory of the device, and an audio file can be selected from the plurality of audio files based on a type of the waveform, the sound being generated based on the audio file.

Figure 9:
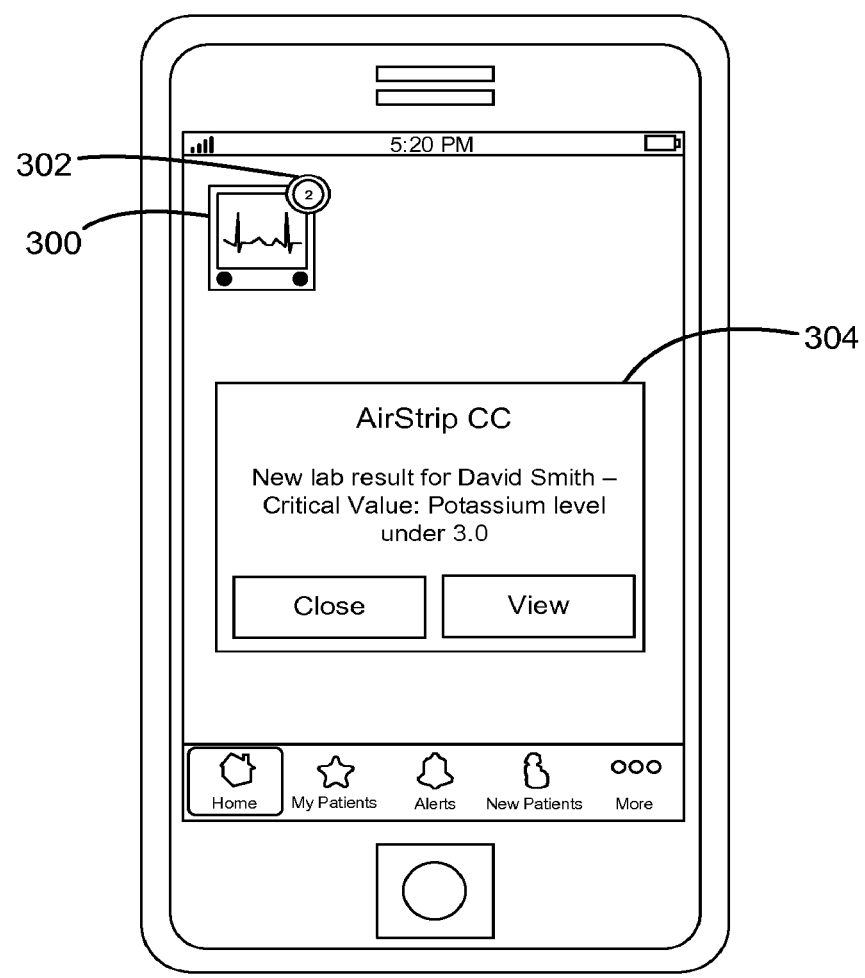
FIG. 9 provides an exemplar screenshot illustrating a push-notification feature in accordance with the present disclosure.
Figure 10:
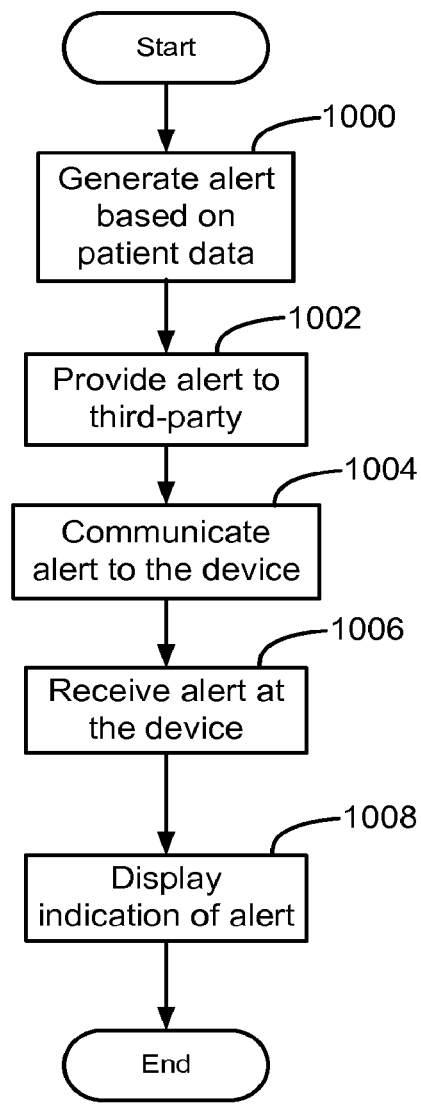
FIG. 10 is a flowchart illustrating exemplar steps that can be executed to provide push-notification of patient data alerts in accordance with the present disclosure.

Referring now to FIGS. 9 and 10, a push-notification feature is provided. More specifically, routines can be executed at the DMS 60, 60' to analyze and review patient data as it is received from the information system(s) 42, and alerts can be generated based on this analysis and review. In some cases, the information system 42 can analyze and review patient data, and generate alerts based on this analysis and review. These alerts can be pushed to the device 12 using a push-notification infrastructure. More specifically, the alerts resident at the DMS 60, 60' (regardless of whether the alerts were generated at the DMS 60, 60', or the information system 42) can be forwarded to a third-party push notification service, which pushes the alerts to the device 12. In this manner, the underlying application does not have to be running on the device in order to receive such alerts.

With particular reference to FIG. 9, a display of the device 12 includes an application icon 300. In the exemplar illustration of FIG. 9, the application includes AirStrip Critical Care (CC) provided by AirStrip Technologies, LLC. It is appreciated, however, that the application can include any application that is executed on the device 12 to display patient data on the device 12. Such applications can also include, but are not limited to, AirStrip OB, AirStrip Cardiology, AirStrip Laboratory, and/or AirStrip Imaging. The application icon 300 includes a badge 302 that, in the exemplar illustration, indicates that two alerts have been pushed to the device. Upon receiving an alert, the device 12 can display an alert summary 304 that provides relevant patient and alert information. In this manner, the user can decide whether they should immediately view the alert. The badge notification and/or alert summary is automatically generated and/or updated while the underlying application is dormant (i.e., not being executed). In other words, the application does not need to be active and executing on the device 12 in order for the device 12 to receive the alerts. Furthermore, an audible (i.e., sound), or physical (e.g., vibration) indicator can be generated when an alert is received, notifying the user that an alert has been received. This provides significant benefits in that the user can receive the alerts while working in another application on the device 12, and can receive the alerts when not using the device 12 at all.

Referring now to FIG. 10, exemplar steps that can be executed to provide push-notification will be described. In step 1000, an alert is generated based on patient data. In some cases, the alert can be generated at an information system that is resident at a facility, at which the patient data is collected. In some cases, the alert can be generated at a data management system that is remote from the source of the patient data. In step 1002, the alert is provided to a third-party notification service. The alert is communicated to a device, the device being remote from a source of the patient data, in step 1004, and the alert is received at the device in step 1006. The alert can correspond to an application that is resident on the device, and that is executable using the device. The application can be dormant when the alert is received at the device. In step 1008, an indication of the alert is presented on a display of the device. The indication can include at least one of a badge associated with an application icon, and an alert summary. The alert summary can provide patient information. The alert summary can be selected, and detailed alert information can be displayed on the display of the device in response to the selecting.

The present disclosure can be implemented in digital electronic circuitry, or in computer hardware, firmware, software, or in combinations thereof. The invention can be implemented as a computer program product, i.e., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Such a computer program can include modules and/or code segments for executing one or more of the features, aspects and/or implementations provided herein.

Method steps of the present disclosure can be performed by one or more programmable processors executing a computer program product to perform functions of the present disclosure by operating on input data and generating output. By way of one non-limiting example, a computer program product can include modules and/or code segments corresponding to each of the method steps, aspects and/or features provided herein. Method steps can also be performed by, and apparatus of the present disclosure can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks. The processor and the memory can be supplemented by, or incorporated in special purpose logic circuitry.

The present disclosure can be implemented in a system including, but not limited to the exemplar systems described herein, which include a back-end component, e.g., as a data server, or that includes a middleware component, e.g., an application server, or that includes a front-end component, e.g., a client device, such as the remote device 12, having a graphical user interface or a Web browser through which a user can interact with an implementation of the invention, or any combination of such back-end, middleware, or front-end components. The components of the system can be interconnected by any form or medium of digital data communication, e.g., a communication network.

A number of embodiments have been described. Nevertheless, it will be understood that various modifications may be made without departing from the spirit and scope of the disclosure. For example, steps of the invention can be performed in a different order and still achieve desirable results. Accordingly, other embodiments are within the scope of the following claims.

What is claimed is:

1. A method of measuring features of a waveform, comprising:
    receiving patient data at a data management system from a plurality of facilities, the data management system being configured to synchronize the patient data from the plurality of facilities by generating formatted patient data based on the patient data for transfer to and presentation on a handheld device that is remote from the plurality of facilities;
    receiving the formatted patient data at the handheld device from the data management system;
    receiving, by the handheld device, a selection of a portion of the formatted patient data that corresponds to a facility of the plurality of facilities;
    generating, by the handheld device and based on the portion of the formatted patient data, the waveform on a touch-screen display of the handheld device;
    receiving first user input, the first user input being input to the waveform displayed on the touch-screen display and indicating a user-defined first point on the waveform based on user contact with the touch-screen display;
    receiving second user input, the second user input being input to the waveform displayed on the touch-screen display and indicating a user-defined second point on the waveform based on user contact with the touch-screen display, such that the user-defined first point and the user-defined second point correspond to one of a horizontal direction and a vertical direction of measurement;
    in response to receiving the second user input, automatically measuring a distance between the user-defined first point and the user-defined second point along an axis of the waveform;
    displaying, proximal to the waveform, a value corresponding to the distance on the touch-screen display;
    moving at least one of the user-defined first point and the user-defined second point along the axis in response to a user input;
    updating the value in real-time based on movement of the at least one of the user-defined first point and the user-defined second point along the axis; and
    transmitting the value to the facility.

2. The method of claim 1, wherein the value includes a time value.

3. The method of claim 1, wherein the value includes a voltage value.

4. The method of claim 1, further comprising generating a digital caliper in the touch-screen display, the caliper including a first and a second jaw that are movable along the axis, the first point being generated based on an intersection between the first jaw and the waveform, and the second point being generated based on an intersection between the second jaw and the waveform.

5. The method of claim 4, wherein the caliper is generated based on a user demand.

6. The method of claim 1, wherein the axis includes one of a time axis and a voltage axis.

7. The method of claim 1, wherein the waveform corresponds to one of an electrocardiogram (ECG), a blood pressure, an oxygen saturation, and an end-tidal CO2.

8. The method of claim 1, further comprising storing the value in a memory of the handheld device.

9. The method of claim 1, further comprising transmitting the value to a patient information system located at a facility.

10. The method of claim 1, further comprising:
    identifying an occurrence of a waveform feature; and
    generating a sound based on the occurrence of the waveform feature.

11. The method of claim 10, wherein the generating a sound comprises repetitively generating the sound in response to periodic occurrences of the waveform feature.

12. The method of claim 10, wherein the generating a sound comprises generating a persistent sound.

13. The method of claim 10, further comprising:
    storing an audio file in memory of the handheld device; and
    retrieving the audio file from memory based on generating the waveform, the sound being generated based on the audio file.

14. The method of claim 10, further comprising:
    storing a plurality of audio files in memory of the handheld device; and
    selecting an audio file from the plurality of audio files based on a type of the waveform, the sound being generated based on the audio file.

15. The method of claim 10, wherein the waveform feature includes one of a spike, a peak, a trough and a flat line.

16. The method of claim 10, wherein the waveform corresponds to one of a heart rate, a blood pressure, an oxygen saturation, and an end-tidal CO2.

17. The method of claim 1, further, comprising:
    generating an alert based on the patient data;
    providing the alert to a third-party notification service;
    forwarding the alert to the handheld device;
    receiving the alert at the handheld device; and
    presenting an indication of the alert on a display of the handheld device.

18. The method of claim 17, wherein the alert is generated at an information system that is resident at a facility, at which the patient data is collected.

19. The method of claim 17, wherein the alert is generated at the data management system that is remote from the plurality of facilities.

20. The method of claim 17, wherein the alert corresponds to an application that is resident on the handheld device, and that is executable using the handheld device.

21. The method of claim 20, wherein the application is dormant when the alert is received at the handheld device.

22. The method of claim 17, wherein the indication includes at least one of a badge associated with an application icon, and an alert summary.

23. The method of claim 22, wherein the alert summary provides patient information.

24. The method of claim 22, further comprising:
selecting the alert summary; and
displaying detailed alert information on the display of the handheld device in response to the selecting.

25. A non-transitory computer-readable storage medium encoded with a computer program comprising instructions that, when executed, cause one or more processors to perform operations comprising:
receiving patient data at a data management system from a plurality of facilities, the data management system being configured to synchronize the patient data from the plurality of facilities by generating formatted patient data based on the patient data for transfer to and presentation on a handheld device that is remote from the plurality of facilities;
receiving the formatted patient data at the handheld device from the data management system;
receiving, by the handheld device, a selection of a portion of the formatted patient data that corresponds to a facility of the plurality of facilities;
generating, by the handheld device and based on the portion of the formatted patient data, a waveform on a touch-screen display of the handheld device;
receiving first user input, the first user input being input to the waveform displayed on the touch-screen display and indicating a user-defined first point on the waveform based on user contact with the touch-screen display;
receiving second user input, the second user input being input to the waveform displayed on the touch-screen display and indicating a user-defined second point on the waveform based on user contact with the touch-screen display, such that the user-defined first point and the user-defined second point correspond to one of a horizontal direction and a vertical direction of measurement;
in response to receiving the second user input, automatically measuring a distance between the user-defined first point and the user-defined second point along an axis of the waveform;
displaying, proximal to the waveform, a value corresponding to the distance on the touch-screen display;
moving at least one of the user-defined first point and the user-defined second point along the axis in response to a user input;
updating the value in real-time based on movement of the at least one of the user-defined first point and the user-defined second point along the axis; and
transmitting the value to the facility.

26. A system for measuring features of a waveform, the system comprising:
a server system that performs operations comprising:
receiving patient data at a data management system from a plurality of facilities,
transmitting patient data in real-time over a wide area digital network;
a data management system configured to synchronize the patient data from the plurality of facilities by generating formatted patient data based on the patient data for transfer to and presentation on a handheld device; and
the remote-handheld data processing device that is remote from the plurality of facilities, that executes a computer-executable application for measuring features of a digitally generated waveform on a touch-screen display of the remote-handheld data processing device and that performs operations comprising:
receiving the formatted patient data from the data management system;
receiving a selection of a portion of the formatted patient data that corresponds to a facility of the plurality of facilities;
generating based on the portion of the formatted patient data, the waveform on a touch-screen display of the handheld device;
receiving first user input, the first user input being input to the waveform displayed on the touch-screen display and indicating a user-defined first point on the waveform based on user contact with the touch-screen display;
receiving second user input, the second user input being input to the waveform displayed on the touch-screen display and indicating a user-defined second point on the waveform based on user contact with the touch-screen display, such that the user-defined first point and the user-defined second point correspond to one of a horizontal direction and a vertical direction of measurement;
in response to receiving the second user input, automatically measuring a distance between the user-defined first point and the user-defined second point along an axis of the waveform;
displaying, proximal to the waveform, a value corresponding to the distance on the touch-screen display;
moving at least one of the user-defined first point and the user-defined second point along the axis in response to a user input;
updating the value in real-time based on movement of the at least one of the user-defined first point and the user-defined second point along the axis; and
transmitting the value to the facility.

* * * * *